United States Patent
Lee et al.

(10) Patent No.: US 8,105,350 B2
(45) Date of Patent: Jan. 31, 2012

(54) SURGICAL INSTRUMENT

(75) Inventors: Woojin Lee, Hopkinton, MA (US); Andres Chamorro, Waltham, MA (US); Richard C. Fortier, Concord, MA (US); Jeffrey C. Cerier, Franklin, MA (US)

(73) Assignee: Cambridge Endoscopic Devices, Inc., Framingham, MA (US)

( * ) Notice: Subject to any disclaimer, the term of this patent is extended or adjusted under 35 U.S.C. 154(b) by 84 days.

(21) Appl. No.: 11/505,003

(22) Filed: Aug. 16, 2006

(65) Prior Publication Data

US 2007/0276430 A1    Nov. 29, 2007

Related U.S. Application Data

(60) Provisional application No. 60/802,885, filed on May 23, 2006.

(51) Int. Cl.
*A61B 17/00* (2006.01)

(52) U.S. Cl. ....................................................... 606/205

(58) Field of Classification Search .......... 606/139–146, 606/205–206; 446/378; 600/141, 142, 148; 604/528
See application file for complete search history.

(56) References Cited

U.S. PATENT DOCUMENTS

| | | |
|---|---|---|
| 2,028,635 A | 1/1936 | Wappler |
| 2,507,710 A | 5/1950 | Grosso |
| 2,790,437 A | 4/1957 | Moore |
| 3,107,954 A | 10/1963 | Rudy |
| 3,557,780 A | 1/1971 | Sato |
| 3,858,577 A | 1/1975 | Bass et al. |
| 3,895,636 A | 7/1975 | Schmidt |
| 4,483,562 A | 11/1984 | Schoolman |
| 4,483,579 A | 11/1984 | Derr et al. |
| 4,531,855 A | 7/1985 | Wallis |
| 4,554,798 A | 11/1985 | D'Amour et al. |

(Continued)

FOREIGN PATENT DOCUMENTS

EP    0 095 970 A2    12/1983

(Continued)

OTHER PUBLICATIONS

Nakamura et al., Multi-DOF Forceps Manipulator System for Laparoscopic Surgery—Mechanism Miniaturized & Evaluation of New Enterfaces, 5 pgs.

(Continued)

*Primary Examiner* — Gary Jackson
*Assistant Examiner* — Eric Blatt
(74) *Attorney, Agent, or Firm* — David M. Driscoll, Esq.

(57) ABSTRACT

The surgical instrument includes a distal tool, a rigid or flexible elongated shaft that supports the distal tool, and a proximal handle or control member, where the tool and the handle are coupled to the respective distal and proximal ends of the elongated shaft via distal and proximal bendable motion members. Actuation means extends between said distal and proximal members whereby any deflection of said control handle with respect to said elongated instrument shaft causes a corresponding bending of said distal motion member for control of said working member. A manually rotatable member is arranged adjacent to the control handle for manually rotating the instrument shaft and working member relative to the control handle. A locking member is supported from the control handle and has locked and unlocked states; in the unlocked state enabling control of the distal work member from the proximal control handle via the bendable members; and in the locked state, holding the bendable members in a pre-selected relative fixed position.

18 Claims, 9 Drawing Sheets

U.S. PATENT DOCUMENTS

| | | | |
|---|---|---|---|
| 4,688,554 | A | 8/1987 | Habib |
| 4,728,020 | A | 3/1988 | Green et al. |
| 4,763,669 | A | 8/1988 | Jaeger |
| 4,872,456 | A | 10/1989 | Hasson |
| 4,880,015 | A | 11/1989 | Nierman |
| 4,944,093 | A | 7/1990 | Falk |
| 4,944,741 | A | 7/1990 | Hasson |
| 4,945,920 | A | 8/1990 | Clossick |
| 5,002,543 | A | 3/1991 | Bradshaw et al. |
| 5,042,707 | A | 8/1991 | Taheri |
| 5,209,747 | A | 5/1993 | Knoepfler |
| 5,251,611 | A * | 10/1993 | Zehel et al. ............ 600/141 |
| 5,254,130 | A * | 10/1993 | Poncet et al. ............ 606/206 |
| 5,271,381 | A | 12/1993 | Ailinger et al. |
| 5,273,026 | A | 12/1993 | Wilk |
| 5,275,608 | A | 1/1994 | Forman et al. |
| 5,314,424 | A | 5/1994 | Nicholas |
| 5,330,502 | A | 7/1994 | Hassler et al. |
| 5,344,428 | A | 9/1994 | Griffiths |
| 5,383,880 | A | 1/1995 | Hooven |
| 5,386,818 | A | 2/1995 | Schneebaum et al. |
| 5,391,180 | A | 2/1995 | Tovey et al. |
| 5,395,367 | A | 3/1995 | Wilk |
| 5,405,344 | A | 4/1995 | Williamson et al. |
| 5,417,203 | A | 5/1995 | Tovey et al. |
| 5,433,721 | A | 7/1995 | Hooven et al. |
| 5,441,494 | A | 8/1995 | Ortiz |
| 5,454,827 | A | 10/1995 | Aust et al. |
| 5,501,654 | A | 3/1996 | Failla et al. |
| 5,508,712 | A | 4/1996 | Tom et al. |
| 5,520,678 | A | 5/1996 | Heckele et al. |
| 5,556,416 | A | 9/1996 | Clark et al. |
| 5,599,151 | A | 2/1997 | Daum et al. |
| 5,618,294 | A | 4/1997 | Aust et al. |
| 5,624,381 | A * | 4/1997 | Kieturakis ............ 600/206 |
| 5,643,294 | A * | 7/1997 | Tovey et al. ............ 606/148 |
| 5,665,105 | A | 9/1997 | Furnish et al. |
| 5,702,408 | A | 12/1997 | Wales et al. |
| 5,743,496 | A | 4/1998 | Atkinson, Jr. |
| 5,759,151 | A | 6/1998 | Sturges |
| 5,766,196 | A | 6/1998 | Griffiths |
| 5,772,578 | A | 6/1998 | Heimberger et al. |
| 5,823,066 | A | 10/1998 | Huitema et al. |
| 5,827,177 | A | 10/1998 | Oneda et al. |
| 5,851,208 | A | 12/1998 | Trott |
| 5,855,569 | A | 1/1999 | Komi |
| 5,873,817 | A | 2/1999 | Kokish et al. |
| 5,899,425 | A | 5/1999 | Corey Jr. et al. |
| 5,899,914 | A | 5/1999 | Zirps et al. |
| 5,904,647 | A | 5/1999 | Ouchi |
| 5,916,146 | A | 6/1999 | Allotta et al. |
| 5,916,147 | A | 6/1999 | Boury |
| 5,921,956 | A | 7/1999 | Grinberg et al. |
| 5,928,263 | A | 7/1999 | Hoogeboom |
| 5,938,678 | A | 8/1999 | Zirps et al. |
| 5,944,713 | A | 8/1999 | Schuman |
| 5,987,757 | A | 11/1999 | Schmidt et al. |
| 6,126,633 | A | 10/2000 | Kaji et al. |
| 6,147,650 | A | 11/2000 | Kawahata et al. |
| 6,174,280 | B1 | 1/2001 | Oneda et al. |
| 6,210,377 | B1 | 4/2001 | Ouchi |
| 6,210,378 | B1 | 4/2001 | Ouchi |
| 6,210,416 | B1 | 4/2001 | Chu et al. |
| 6,270,453 | B1 | 8/2001 | Sakai |
| 6,352,227 | B1 | 3/2002 | Hathaway |
| 6,551,238 | B2 | 4/2003 | Staud |
| 6,623,424 | B2 | 9/2003 | Hayakawa et al. |
| 6,638,214 | B2 | 10/2003 | Akiba |
| 6,641,316 | B1 | 11/2003 | Goldstein et al. |
| 6,656,195 | B2 | 12/2003 | Peters et al. |
| 6,666,854 | B1 | 12/2003 | Lange |
| 6,752,756 | B2 | 6/2004 | Lunsford et al. |
| 6,761,717 | B2 | 7/2004 | Bales et al. |
| 6,889,116 | B2 | 5/2005 | Jinno |
| 7,073,822 | B1 | 7/2006 | Renfroe et al. |
| 7,090,637 | B2 | 8/2006 | Danitz |
| 7,147,650 | B2 | 12/2006 | Lee |
| 7,320,700 | B2 | 1/2008 | Cooper et al. |
| 7,338,513 | B2 | 3/2008 | Lee et al. |
| 7,364,582 | B2 | 4/2008 | Lee |
| 7,615,067 | B2 | 11/2009 | Lee et al. |
| 7,648,519 | B2 | 1/2010 | Lee et al. |
| 7,678,117 | B2 | 3/2010 | Hinman et al. |
| 7,682,307 | B2 | 3/2010 | Danitz et al. |
| 7,686,826 | B2 | 3/2010 | Lee et al. |
| 7,708,758 | B2 | 5/2010 | Lee et al. |
| 7,785,252 | B2 | 8/2010 | Danitz et al. |
| 7,842,028 | B2 | 11/2010 | Lee |
| 2002/0045803 | A1 | 4/2002 | Abe et al. |
| 2002/0095175 | A1 | 7/2002 | Brock et al. |
| 2002/0133173 | A1 | 9/2002 | Brock et al. |
| 2002/0156497 | A1 | 10/2002 | Nagase et al. |
| 2002/0177750 | A1 | 11/2002 | Pilvisto |
| 2002/0177847 | A1 | 11/2002 | Long |
| 2003/0065359 | A1 | 4/2003 | Weller et al. |
| 2003/0109898 | A1 | 6/2003 | Schwarz et al. |
| 2003/0135204 | A1 | 7/2003 | Lee et al. |
| 2003/0149338 | A1 | 8/2003 | Francois et al. |
| 2003/0171650 | A1 * | 9/2003 | Tartaglia et al. ............ 600/114 |
| 2003/0216618 | A1 | 11/2003 | Arai |
| 2003/0216619 | A1 | 11/2003 | Scirica et al. |
| 2003/0225364 | A1 | 12/2003 | Kraft et al. |
| 2004/0049205 | A1 | 3/2004 | Lee et al. |
| 2004/0111009 | A1 | 6/2004 | Adams et al. |
| 2004/0138529 | A1 | 7/2004 | Wiltshire et al. |
| 2004/0176751 | A1 | 9/2004 | Weitzner et al. |
| 2004/0193146 | A1 | 9/2004 | Lee et al. |
| 2004/0236316 | A1 | 11/2004 | Danitz et al. |
| 2005/0049580 | A1 | 3/2005 | Brock et al. |
| 2005/0096694 | A1 * | 5/2005 | Lee ............ 606/205 |
| 2005/0107667 | A1 | 5/2005 | Danitz et al. |
| 2005/0228440 | A1 | 10/2005 | Brock et al. |
| 2005/0251112 | A1 | 11/2005 | Danitz et al. |
| 2005/0273084 | A1 * | 12/2005 | Hinman et al. ............ 606/1 |
| 2005/0273085 | A1 | 12/2005 | Hinman et al. |
| 2006/0095074 | A1 | 5/2006 | Lee et al. |
| 2006/0195097 | A1 | 8/2006 | Evans et al. |
| 2006/0206101 | A1 | 9/2006 | Lee |
| 2006/0270909 | A1 | 11/2006 | Davis et al. |
| 2007/0021737 | A1 | 1/2007 | Lee |
| 2007/0250110 | A1 | 10/2007 | Lu et al. |
| 2007/0276430 | A1 | 11/2007 | Lee et al. |
| 2008/0255420 | A1 | 10/2008 | Lee et al. |
| 2008/0294191 | A1 | 11/2008 | Lee |
| 2009/0069842 | A1 | 3/2009 | Lee et al. |
| 2009/0171147 | A1 | 7/2009 | Lee et al. |

FOREIGN PATENT DOCUMENTS

| | | |
|---|---|---|
| EP | 0 448 284 A2 | 9/1991 |
| EP | 0 626 604 A2 | 5/1994 |
| EP | 0 427 949 B1 | 6/1994 |
| GB | 2 143 920 | 2/1985 |
| JP | 2002 102248 | 4/2002 |
| JP | 2003 135473 | 5/2003 |
| WO | WO 90/05491 | 5/1990 |
| WO | WO 92/01414 | 2/1992 |
| WO | WO 94/17965 | 8/1994 |
| WO | 97 23158 | 7/1997 |
| WO | 02 13682 | 2/2002 |
| WO | 2004 105578 | 12/2004 |

OTHER PUBLICATIONS

Ryoichi Nakamura et al., Multi-DOF Manipulator System for Laparoscopic Surgery, 8 pgs.

Ryoichi Nakamura et al., Development of Forceps Manipulator System for Laparoscopic Surgery, 6 pgs.

Hiromasa Yamashita et al., "Multi-Slider Linkage Mechanism for Endoscopic Forceps Manipulator," In Proc. of the 2003 IEEE/RSJ, Intl. Conference on Intelligent Robots and Systems, vol. 3, pp. 2577-2582, Las Vegas, Nevada, Oct. 2003.

* cited by examiner

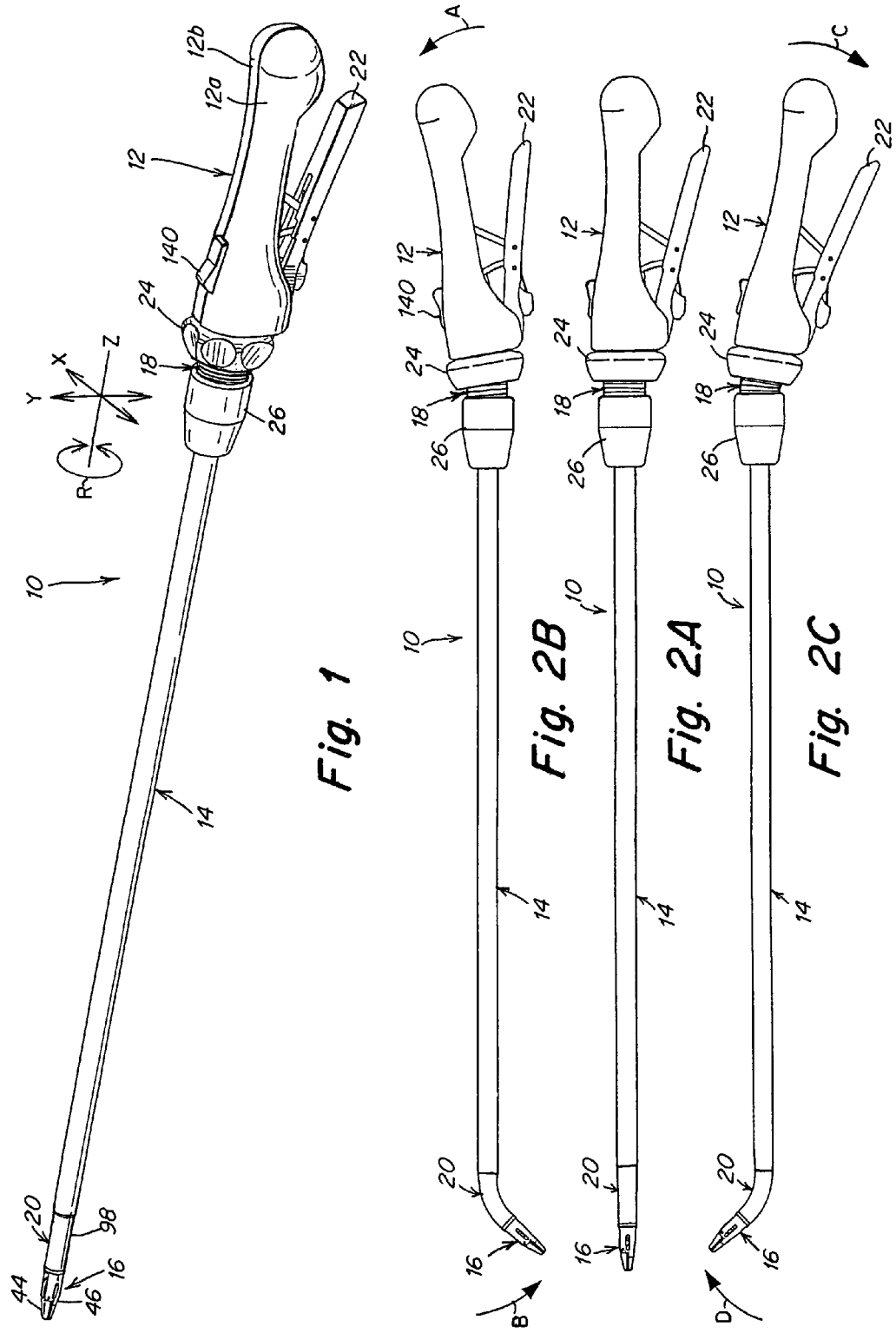

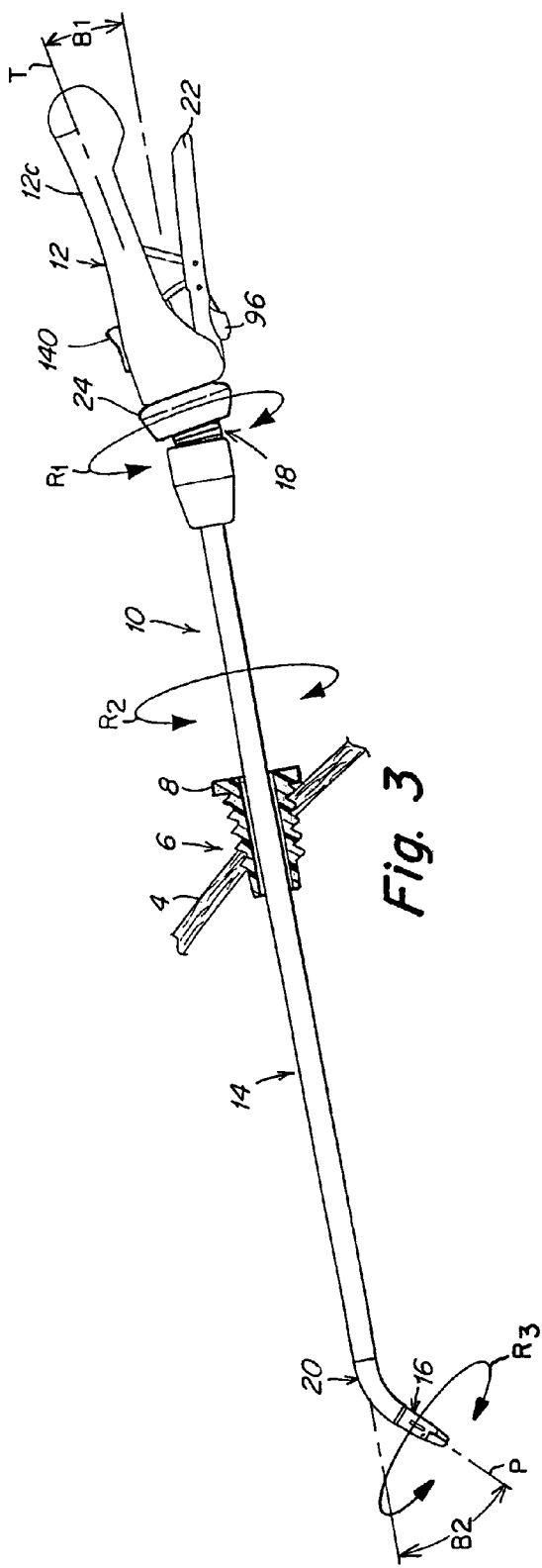
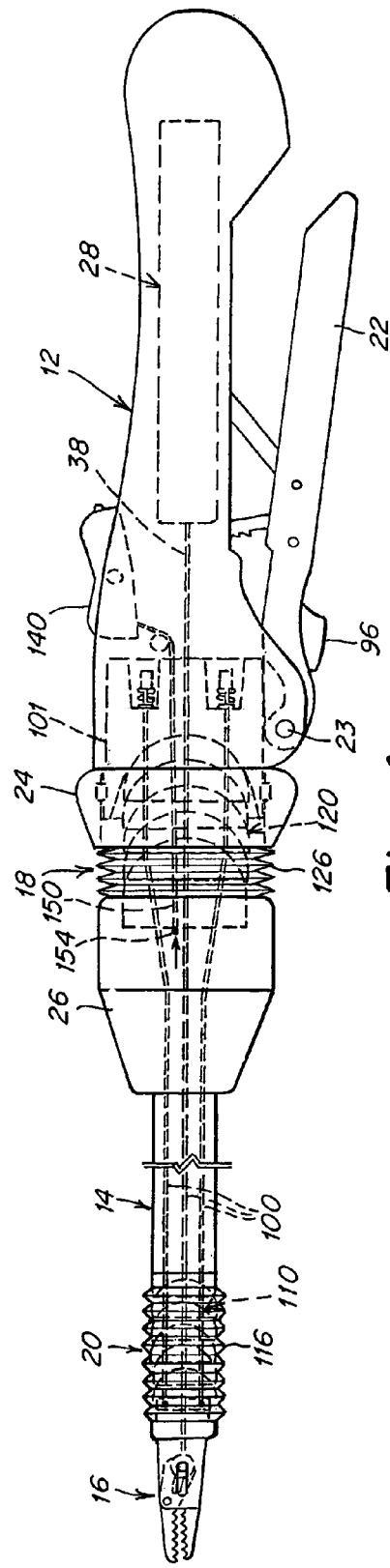
Fig. 3
Fig. 4

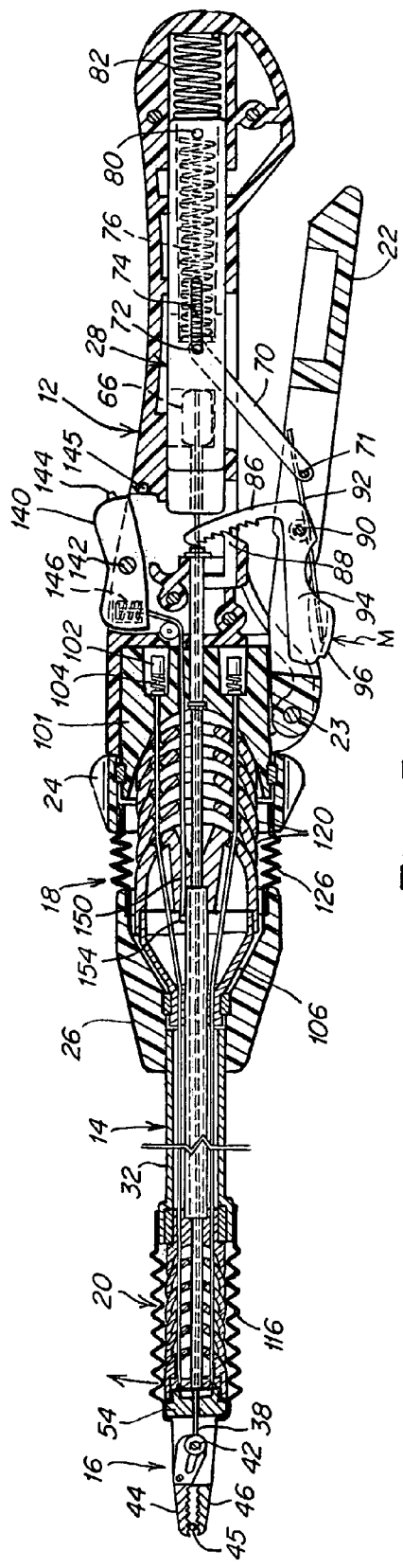
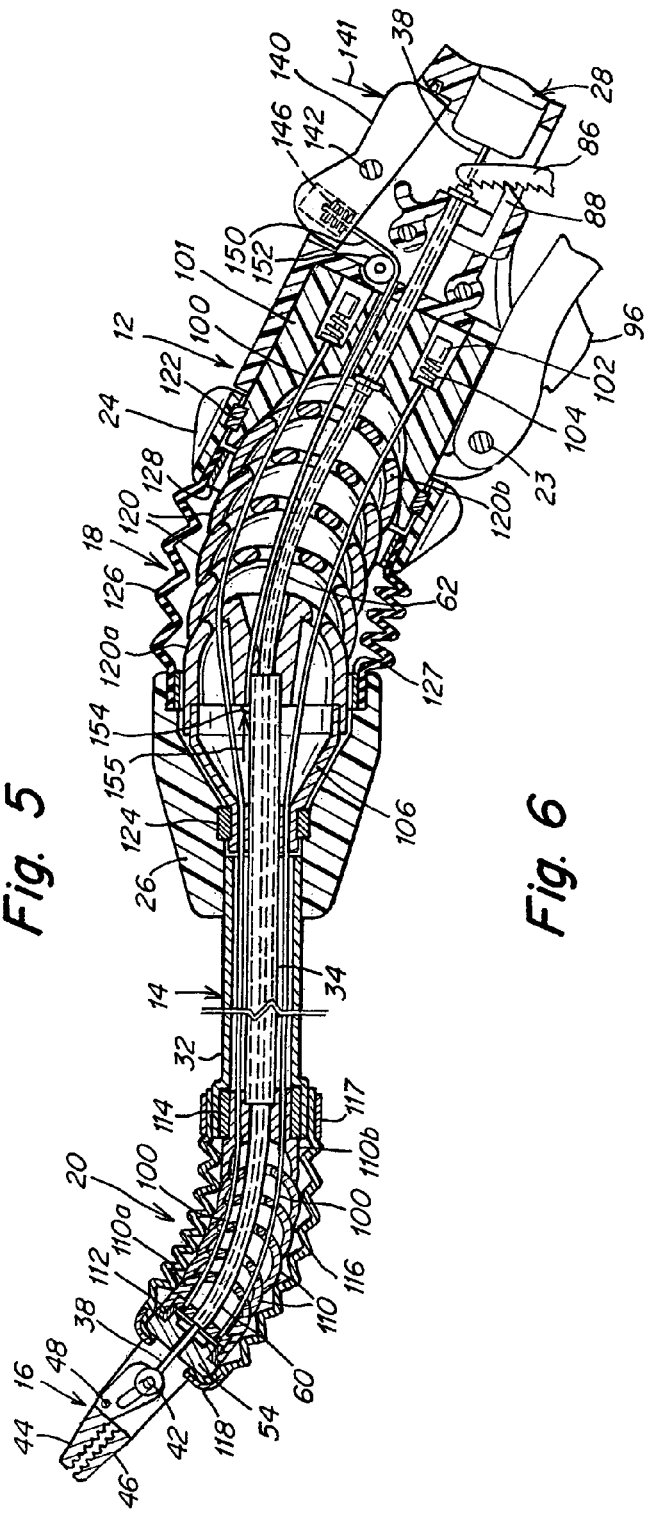
Fig. 5
Fig. 6

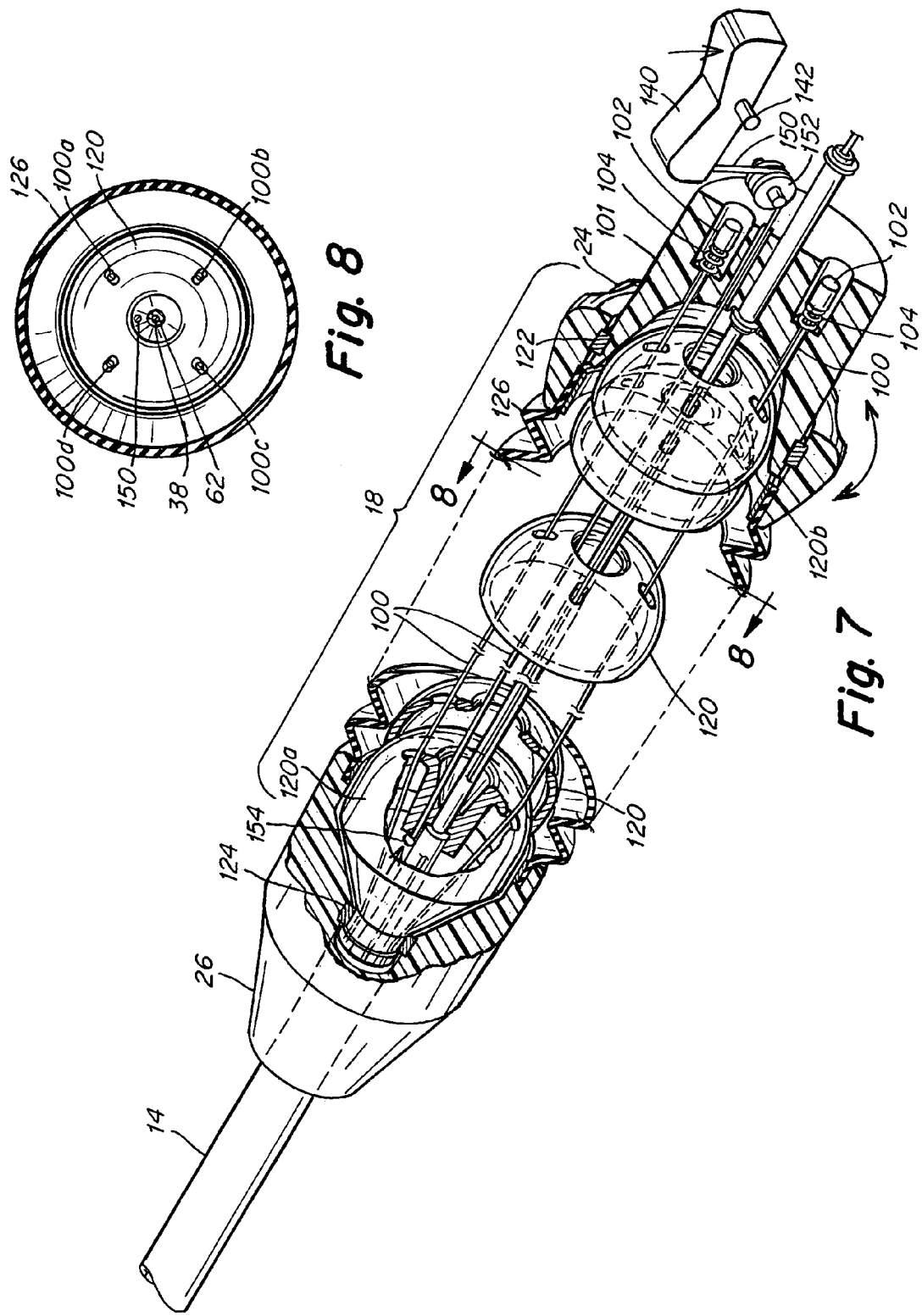

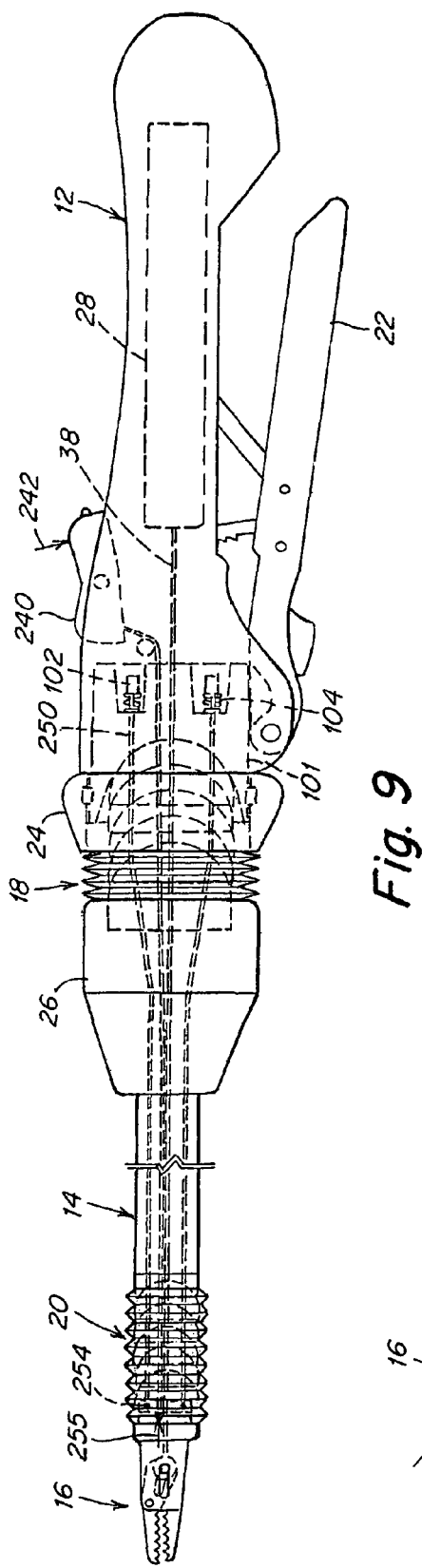
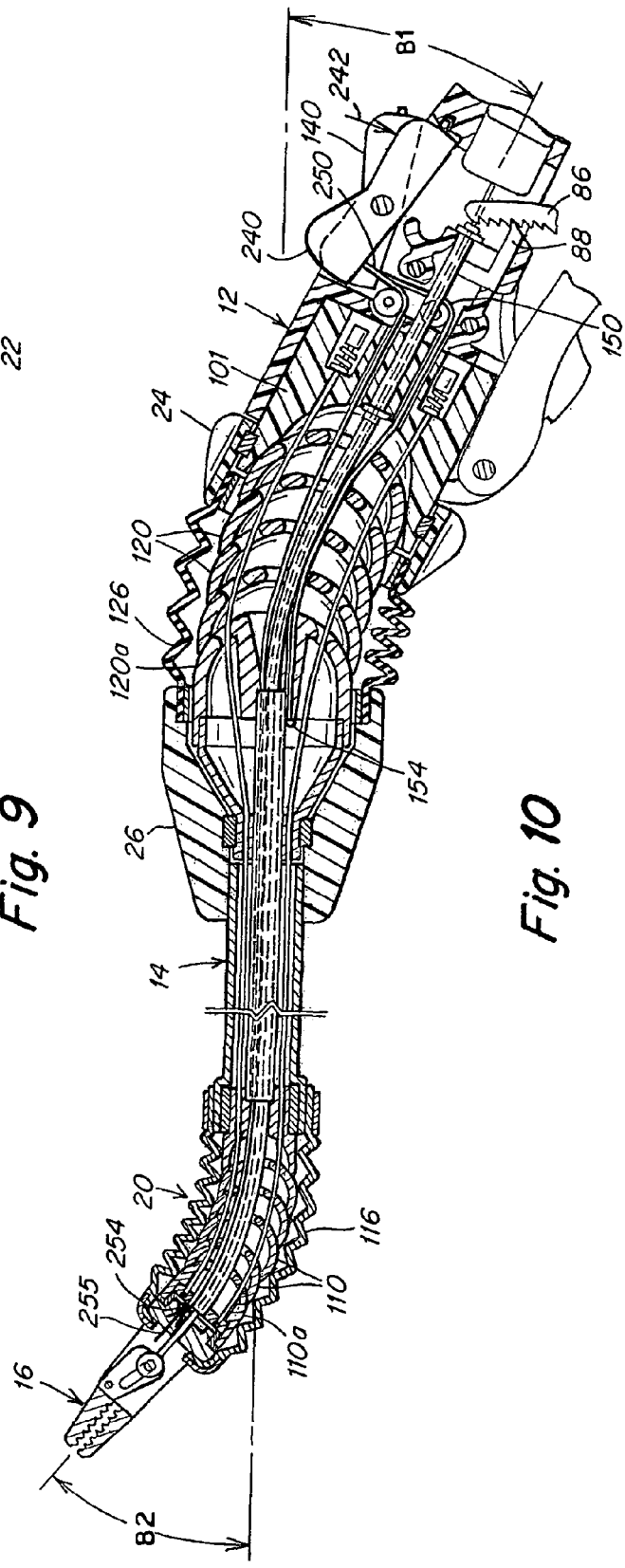
Fig. 9
Fig. 10

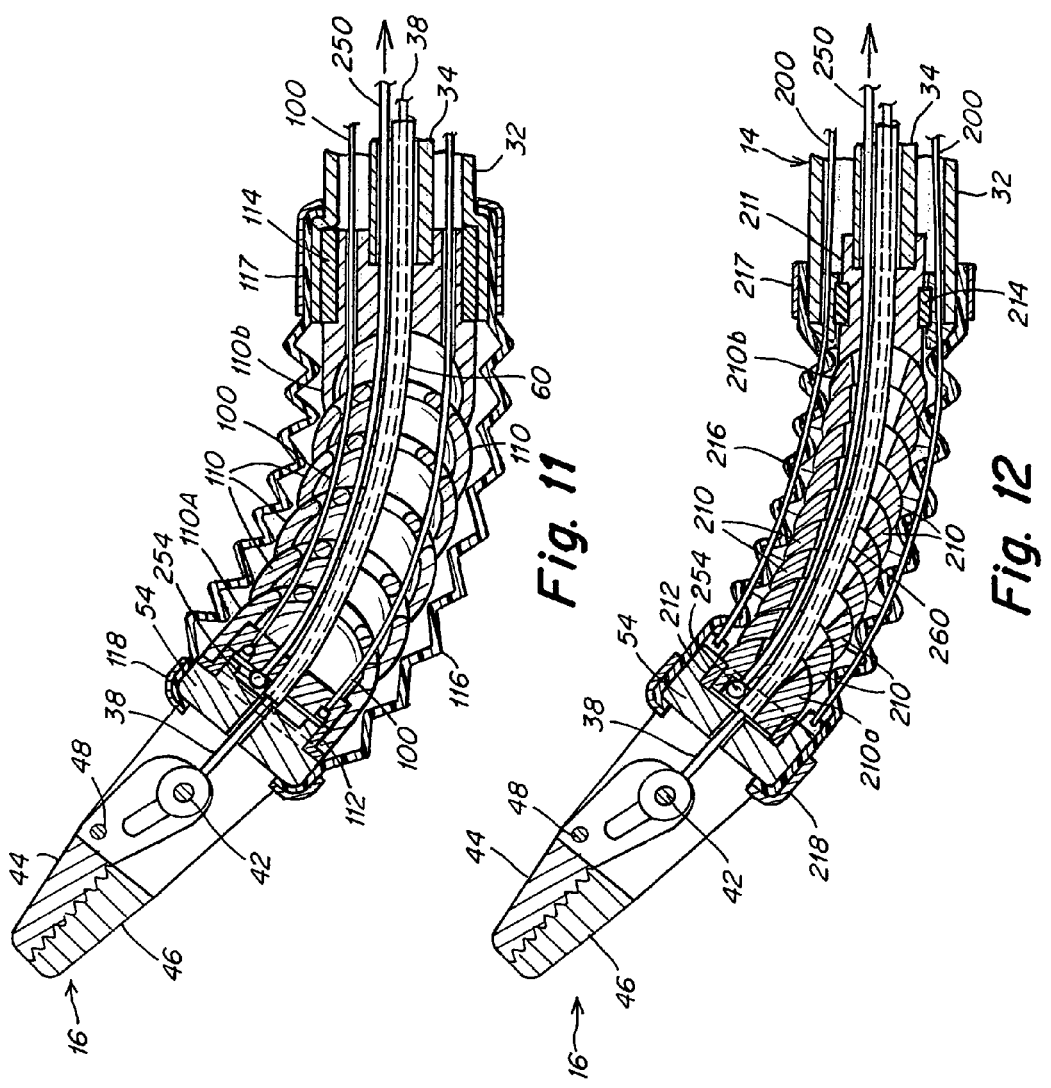

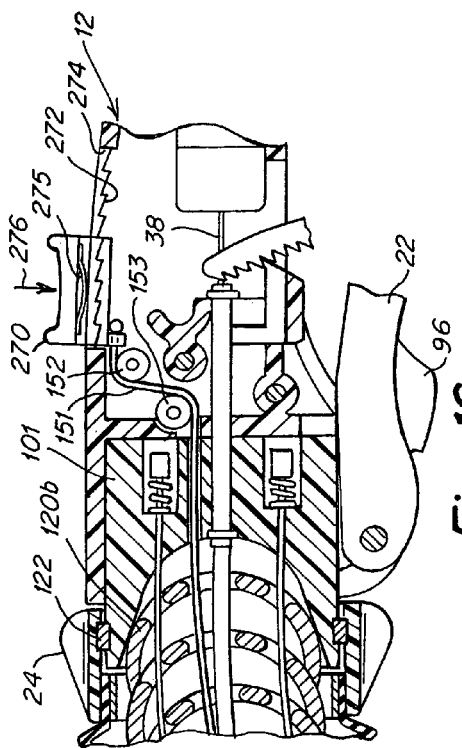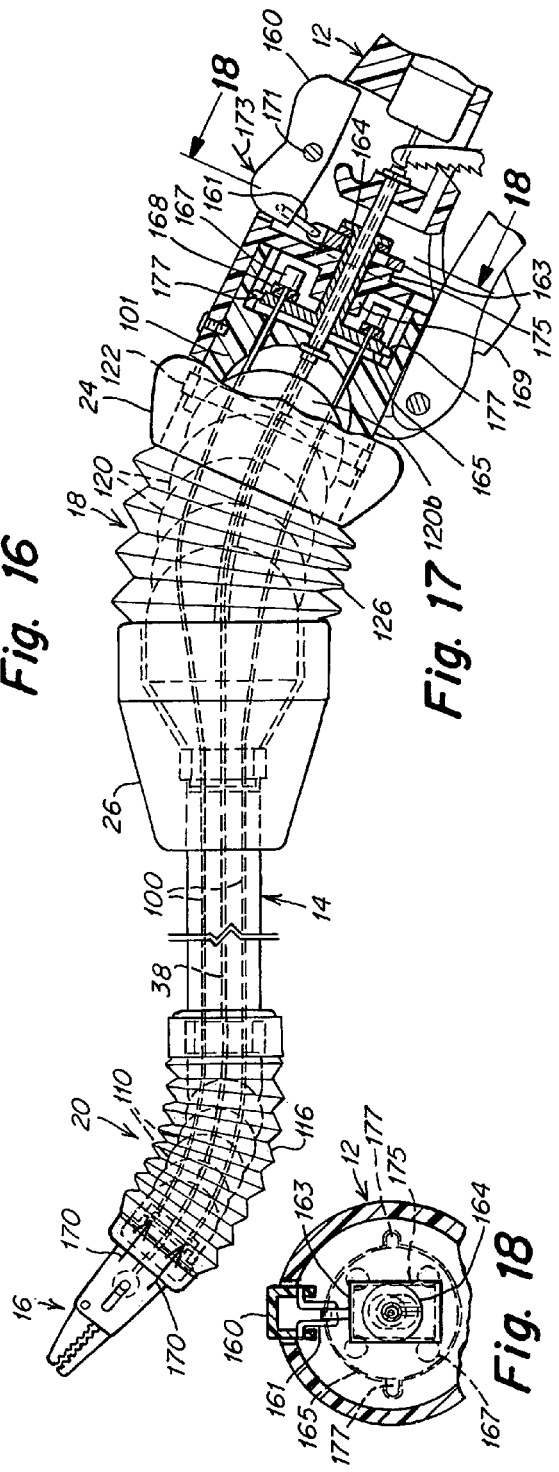

SURGICAL INSTRUMENT

RELATED APPLICATION

The present application claims priority to U.S. Provisional Application Ser. No. 60/802,885 filed on May 23, 2006. The content of all of the aforementioned application is hereby incorporated by reference herein in its entirety.

TECHNICAL FIELD

The present invention relates in general to surgical instruments, and more particularly to manually-operated surgical instruments that are intended for use in minimally invasive surgery or other forms of surgical or medical procedures or techniques. The instrument described herein is primarily for laparoscopic or endoscopic procedures, however, it is to be understood that the instrument of the present invention can be used for a wide variety of other procedures, including intraluminal procedures.

BACKGROUND OF THE INVENTION

Endoscopic and laparoscopic instruments currently available in the market are extremely difficult to learn to operate and use, mainly due to a lack of dexterity in their use. For instance, when using a typical laparoscopic instrument during surgery, the orientation of the tool of the instrument is solely dictated by the locations of the target and the incision. These instruments generally function with a fulcrum effect using the patients own incision area as the fulcrum. As a result, common tasks such as suturing, knotting and fine dissection have become challenging to master. Various laparoscopic instruments have been developed over the years to overcome this deficiency, usually by providing an extra articulation often controlled by a separately disposed control member for added control. However, even so these instruments still do not provide enough dexterity to allow the surgeon to perform common tasks such as suturing, particularly at any arbitrarily selected orientation. Also, existing instruments of this type do not provide an effective way to hold the instrument in a particular position.

Accordingly, an object of the present invention is to provide an improved laparoscopic or endoscopic surgical instrument that allows the surgeon to manipulate the tool end of the surgical instrument with greater dexterity.

Another object of the present invention is to provide an improved surgical instrument that has a wide variety of applications, through incisions, through natural body orifices or intraluminally.

A further object of the present invention is to provide an improved medical instrument that is characterized by the ability to lock the instrument in a particular position.

Another object of the present invention is to provide a locking feature that is an important adjunct to the other controls of the instrument enabling the surgeon to lock the instrument once in the desired position. This makes it easier for the surgeon to thereafter perform surgical procedures without having to, at the same time, hold the instrument in a particular bent configuration.

Still another object of the present invention is to provide an improved surgical instrument that can be locked in a particular position and yet is rotatable in the locked position about a distal tool axis.

SUMMARY OF THE INVENTION

To accomplish the foregoing and other objects, features and advantages of the present invention there is provided a medical instrument that comprising a proximal control handle; a distal work member; a proximal turnable member controlled from the proximal control handle; a distal turnable member controlled from the proximal turnable member to provide controlled movement of the distal work member from the proximal control handle; an instrument shaft that intercouples the proximal and distal turnable members; and a locking member supported from the proximal control handle and having locked and unlocked states. The locking member, in its unlocked state enables control of the distal work member from the proximal control handle via the turnable members. The locking member, in its locked state, holds the turnable members in a pre-selected relative fixed position.

In accordance with other aspects of the present invention at least one of the turnable members may comprise a bendable member; alternatively both of the turnable members may be bendable members; the locking member, in the locked state, fixes the position of the proximal turnable member; the locking member, in the locked state, may also fix the position of the distal turnable member. First cable means may be provided between the proximal and distal turnable members for providing control therebetween and second cable means may be coupled from the locking member to control at least one of the proximal and distal turnable members. A pair of locking members may be provided for respectively controlling the proximal and distal turnable members. A rotation control member may be disposed adjacent the proximal control handle for controlling the distal work member to rotate about a distal axis.

In accordance with still other aspects of the present invention the instrument is comprised of coaxial inner and outer instrument sections with the outer instrument section including at least the rotation member and work member, the outer instrument section being mounted for rotation relative to the inner instrument section, and the inner instrument section including at least one of the bendable members. The instrument shaft may include an outer sheath that forms part of the outer instrument section and an inner sheath that forms part of the inner instrument section, the outer sheath being mounted for rotation relative to a non-rotatable inner sheath. Cable means may be disposed between the proximal and distal turnable members. The cable means may form part of the outer instrument section and rotates therewith, or may form part of the inner instrument section and is non-rotatable. First cable means may be provided between the proximal and distal turnable members for providing control therebetween and a carriage for supporting the proximal ends of the cable means, the locking member controlling the carriage. The cable means may comprise a plurality of cables that are all attached to the carriage and that are pulled in unison under control of the locking member. Each turnable member may comprise a bendable member that includes a plurality of nestable discs and an outer bellows. The instrument shaft may be flexible for intraluminal use.

In accordance with another embodiment of the present invention there is provided a medical instrument having a proximal control handle and a distal tool that are intercoupled by an elongated instrument shaft that is meant to pass internally of an anatomic body, proximal and distal bendable members that respectively intercouple the proximal control handle and the distal tool with the instrument shaft, and a locking member that is manually operable by a user and is adapted to lock the position of the bendable members in a desired position, the locking member having locked and unlocked states, and a rotation control member manually controllable to rotate the tool about a distal tool axis, the rotation control member operable in at least the locked state of the locking member to rotate the tool about the distal tool axis.

In accordance with still other aspects of the present invention there is provided a medical instrument including cable means coupled from the locking member and for locking at least one of the proximal and distal bendable members in a desired fixed position; an outer sheath may extend between the rotation control member and the distal tool, with the rotation control member being controllable to rotate the tool about the distal tool axis via the outer sheath; control cables may be disposed between the proximal and distal bendable members and further including means for supporting the proximal ends of the cables and constructed and arranged to move the cables in response to the locking member; wherein the support means for the cables may comprise a carriage and the locking member may be constructed and arranged to move the carriage to pull the cables in unison; wherein the instrument shaft may be flexible for intraluminal use; wherein the rotation control member is operable in both the locked and unlocked states of the locking member to rotate the tool about the distal tool axis; wherein the instrument is comprised of coaxial inner and outer instrument sections, said outer instrument section including at least said rotation control member and tool, said outer instrument section being mounted for rotation relative to said inner instrument section, said inner instrument section including at least one of said bendable members; including control cables between the proximal and distal bendable members; and wherein the proximal ends of the control cables are supported at the handle or alternatively at the rotation control member.

In accordance with another embodiment of the present invention there is provided a surgical instrument comprising: an elongated instrument shaft having proximal and distal ends; a tool disposed at the distal end of the instrument shaft; and a control handle disposed at the proximal end of the instrument shaft; the tool being coupled to the distal end of the elongated instrument shaft via a distal bendable member; the control handle coupled to the proximal end of the elongated instrument shaft via a proximal bendable member; actuation means extending between the distal and proximal bendable members whereby any deflection of the control handle with respect to the elongated instrument shaft causes a corresponding bending of the distal motion member for control of the tool; and locking means for controlling the actuation means to hold the bendable members in a pre-selected position.

In accordance with still further aspects of the present invention the actuation means may comprise cable means; the cable means may comprise a plurality of separate cables and the locking means may comprise a carriage for supporting a proximal end of each cable; the locking means may further include a lever and a wedge member that moves in response to the lever to, in turn, control the carriage; including a rotation control member adjacent the control handle for controlling the tool to rotate about a distal tool axis; wherein the instrument is comprised of coaxial inner and outer instrument sections, the outer instrument section including at least the rotation member and tool, the outer instrument section being mounted for rotation relative to the inner instrument section, and the inner instrument section including at least one of the bendable members; wherein the instrument shaft includes an outer sheath that forms part of the outer instrument section and an inner sheath that forms part of the inner instrument section, the outer sheath being mounted for rotation relative to a non-rotatable inner sheath; wherein each bendable member includes a plurality of nestable discs and an outer bellows; and wherein the instrument shaft may be flexible for intraluminal use.

BRIEF DESCRIPTION OF THE DRAWINGS

It should be understood that the drawings are provided for the purpose of illustration only and are not intended to define the limits of the disclosure. The foregoing and other objects and advantages of the embodiments described herein will become apparent with reference to the following detailed description when taken in conjunction with the accompanying drawings in which:

FIG. 1 is a perspective view of a preferred embodiment of the surgical instrument of the present invention;

FIGS. 2A, 2B and 2C are sequential side views of one embodiment of the surgical instrument wherein the distal bendable member bends in the same direction as the proximal bendable member;

FIG. 3 is a schematic side view of the surgical instrument depicted in FIGS. 1 and 2 illustrating the instrument extending through an incision and adapt to be controlled by a surgeon to lock the instrument and to roll the instrument tool about its longitudinal or Z axis;

FIG. 4 is a side elevation view of the surgical instrument of FIG. 1 with the lock member unlocked;

FIG. 5 is a longitudinal cross-sectional side view of the instrument illustrated in FIGS. 1-4 in an unlocked and straight position;

FIG. 6 is a somewhat enlarged fragmentary cross-sectional view of the instrument of FIG. 5 with the instrument in a bent and locked position;

FIG. 7 is an exploded perspective view of the instrument in FIGS. 1-6 taken at the proximal bendable member;

FIG. 8 is a cross-sectional view taken along line 8-8 of FIG. 7;

FIG. 9 is a side elevation view of a second embodiment of the instrument using a locking member that locks the distal motion member;

FIG. 10 is a side elevation cross-sectional view of a third embodiment of the instrument of the present invention in which there is provided both proximal and distal locking members;

FIG. 11 is a fragmentary enlarged cross-sectional view at the end effector and distal bendable member of the embodiment of FIG. 10;

FIG. 12 is a fragmentary enlarged cross-sectional view of a fourth embodiment of the instrument at the end effector and distal bendable member;

FIG. 16 is a fragmentary cross-sectional view of an alternate locking member;

FIG. 17 is a side elevation cross-sectional view of a further embodiment of the present invention in which all control cables are used to lock the instrument; and FIG. 18 is a cross-sectional view taken along line 18-18 of FIG. 17.

DETAILED DESCRIPTION OF THE PREFERRED EMBODIMENT

Figure 7A:
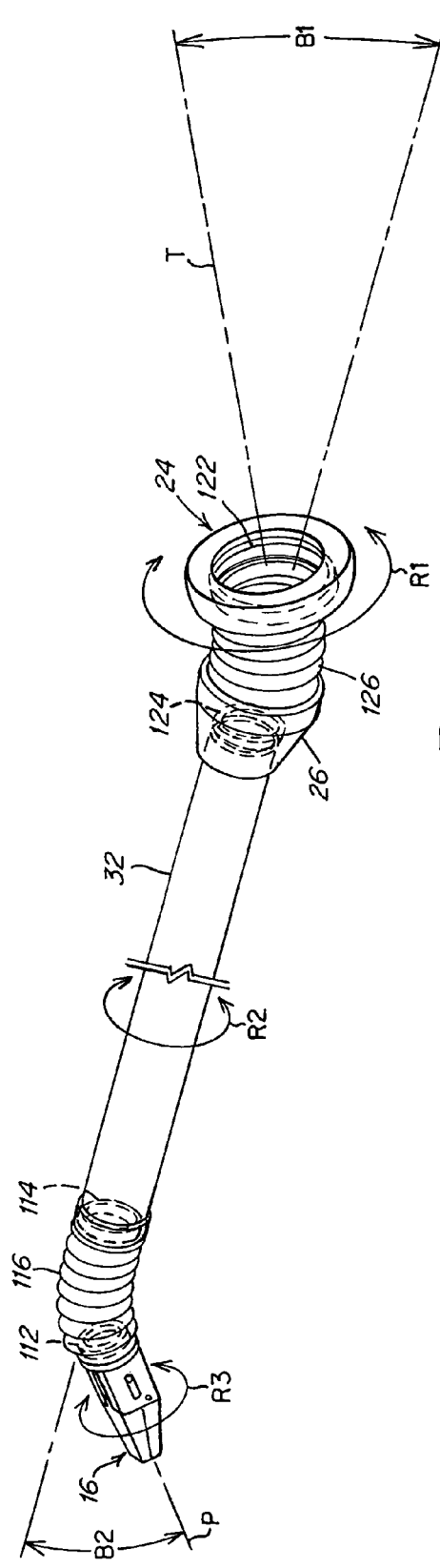
FIGS. 7A and 7B are schematic diagrams of the instrument shown in FIGS. 4-6 illustrating, respectively, inner and outer instrument sections.

The instrument of the present invention may be used to perform minimally invasive procedures. "Minimally invasive procedure," refers herein to a surgical procedure in which a surgeon operates through small cut or incision, the small incision being used to access the operative site. In one embodiment, the incision length ranges from 1 mm to 20 mm in diameter, preferably from 5 mm to 10 mm in diameter. This procedure contrasts those procedures requiring a large cut to access the operative site. Thus, the flexible instrument is preferably used for insertion through such small incisions and/or through a natural body lumen or cavity, so as to locate the instrument at an internal target site for a particular surgical or medical procedure. The introduction of the surgical instrument into the anatomy may also be by percutaneous or surgical access to a lumen or vessel, or by introduction through a natural orifice in the anatomy.

In addition to use in a laparoscopic procedure, the instrument of the present invention may be used in a variety of other medical or surgical procedures including, but not limited to, colonoscopic, upper GI, arthroscopic, sinus, thoracic, transvaginal and cardiac procedures. Depending upon the particular procedure, the instrument shaft may be rigid, semi-rigid or flexible.

Although reference is made herein to a "surgical instrument," it is contemplated that the principles of this invention also apply to other medical instruments, not necessarily for surgery, and including, but not limited to, such other implements as catheters, as well as diagnostic and therapeutic instruments and implements.

FIG. 1 is a perspective view of a preferred embodiment of the surgical instrument 10 of the present invention. In this surgical instrument both the tool and handle motion members or bendable members are capable of bending in any direction. They are interconnected via cables in such a way that a bending action at the proximal member provides a related bending at the distal member. The proximal bending is controlled by a motion or deflection of the control handle by a user of the instrument. In other words the surgeon grasps the handle and once the instrument is in position, such as shown in FIG. 3, any motion at the handle (deflection) immediately controls the proximal bendable member which, in turn, via cabling controls a corresponding bending or deflection at the distal bendable member.

As will be described in further detail hereinafter, the proximal member is preferably larger than the distal member so as to provide enhanced ergonomic control. FIGS. 2a-2c show a bending action in which the distal bendable member bends in the same direction as the proximal bendable member. In an alternate embodiment the bendable, turnable or flexible members may be arranged to bend in opposite directions by rotating the actuation cables through 180 degrees, or could be controlled to bend in virtually any other direction depending upon the relationship between the distal and proximal support points for the cables.

It should be noted that the amount of bending motion produced at the distal bending member is determined by the dimension of the proximal bendable member in comparison to that of the distal bendable member. In the disclosed embodiment the proximal bendable member is at least two times the diameter of the distal bendable member, and as a result, the magnitude of the motion produced at the distal bendable member is greater than the magnitude of the motion at the proximal bendable member. Although FIGS. 2 and 3 show only the side view where only pitch motion is illustrated, it should be noted that the proximal bendable member can be bent in any direction (about 360 degrees) controlling the distal bendable member to bend in either the same or an opposite direction, but in the same plane at the same time. Also, as depicted in FIG. 3, the surgeon is able to bend and roll the instrument's tool about its longitudinal axis at any orientation simply by rolling the axial rotation knob 24.

In this description reference is made to bendable members. These members may also be referred to as turnable members or flexible members. In the descriptions set out herein, terms such as "bendable section," "bendable segment," "bendable motion member," or "turnable member" refer to an element of the instrument that is controllably bendable in comparison to an element that is pivoted at a joint. The bendable elements of the present invention enable the fabrication of an instrument that can bend in any direction without any singularity and that is further characterized by a ready capability to bend in any direction. A definition of these bendable motion members is—an instrument element, formed either as a controlling means or a controlled means, and that is capable of being constrained by tension or compression forces to deviate from a straight line to a curved configuration without any sharp breaks or angularity—.

Referring to FIG. 1, the surgical instrument 10 is comprised of a handle 12 at the proximal end of the instrument, an elongated instrument shaft 14 and a tool or end effector 16 disposed at the distal end of the surgical instrument. The tool may take on a number of different configurations including, but not limited to, articulating and non-articulating tools. In the disclosed embodiment the instrument shaft 14 is rigid, usually of a metal material, although it may also be constructed so as to be at least partially inherently flexible or bendable. For normal laproscopic procedures the instrument shaft 14 is usually rigid. For an example of a flexible instrument shaft used intraluminally refer herein to FIGS. 14 and 15 of related U.S. application Ser. No. 10/822,081, filed on Apr. 12, 2004 which is hereby incorporated by reference herein in its entirety. Also incorporated by reference in their entirety is Ser. No. 11/185,911 filed on Jul. 20, 2005; Ser. No. 11/242,642 filed on Oct. 3, 2005 and Ser. No. 11/302,654 filed on Dec. 14, 2005.

In FIG. 1 the handle 12 is illustrated as comprised of two handle halves 12a and 12b. A lever 22 is manipulatable by the surgeon as the handle is grasped for opening and closing the end effector 16 at the distal end of the instrument shaft 14. In FIG. 1 the end effector is illustrated as comprised of a movable jaw 44 and a fixed jaw 46. The rotation knob 24 at the proximal end of the instrument is used to rotate the instrument shaft and end effector. This rotation is illustrated in FIG. 1 by the circular arrow R. Also note in FIG. 1 the illustration of a coordinate system expressed by the X-Y-Z axes. The roll of the instrument indicated by the arrow R is about the Z axis. The Z axis corresponds to the longitudinal axis of the shaft 14 of the instrument 10.

FIG. 1 also illustrates an adaptor cover 26 for partially retaining a portion of the proximal bendable member 18. At the distal end of the instrument shaft 14, there is provided the distal motion or bendable member 20. In FIG. 1 this is illustrated at least partially covered by the sheath-like cover 98. The cover 98 may be a thin plastic or rubber flexible tube that readily deflects as the distal bendable member is actuated from the proximal bendable member via the handle. For instruments such as a needle holder or a suture assist device, the compliant cover 98 is beneficial in preventing the suture from catching while tying a knot. However, for other applications one may choose not to use the cover 98 so as to simplify the instrument and its fabrication. Other components, such as the knob 24, adaptor cover 26 and bendable members are preferably formed of a plastic material.

The instrument of the present invention is preferably constructed to be disposable or alternatively resposable. Accordingly, to make the instrument as inexpensively as possible most of the components are made of a plastic material.

FIGS. 2A-2C depict one embodiment for the surgical instrument in which the handle and end effector are controlled to turn or bend in the same direction. If the handle is turned upwardly then the tool turns upwardly and vice-versa. FIG. 2A shows the handle in a straight position and the corresponding tool in a likewise straight position. FIG. 2B illustrates the handle end of the instrument having been moved upwardly in the direction of arrow A. This causes a corresponding movement downwardly of the end effector 16 in the direction of arrow B. Similarly, FIG. 2C illustrates the handle 12 being moved downwardly in the direction of arrow C causing a corresponding movement upwardly of the end effector 16 in the direction of arrow D. The bending forces depicted in FIGS. 2B and 2C are imposed upon the proximal bendable member 18 from the handle 12 and when the proximal bendable member is bent or turned, this causes a corresponding bending or turning of the distal bendable member so as to control the position of and orient the end effector. The bending forces are imposed at the handle of the instrument by the surgeon moving the handle in the desire direction and are conveyed to the proximal bendable member, and, in turn, to the distal bendable member. Also, although FIGS. 2A-2C only depict "up" and "down" movement essentially in the plane of the paper, it is understood that the handle can be actuated in any direction (about 360 degrees) including planes in and out of the paper.

FIG. 3 depicts the surgical instrument 10 in position, as may occur during a surgical procedure. For example, the instrument may be used for laproscopic surgery through the abdominal wall 4. For this purpose there is provided an insertion site 6 at which there is disposed a cannula or trocar 8. The shaft of the instrument 14 is adapted to pass through the cannula 8 so as to dispose the distal end of the instrument at an operative site. The end effector 16 is depicted in FIG. 4 at such an operative site. FIG. 3 also depicts the rolling motion that can be carried out with the instrument of the present invention. This can occur by virtue of the rotation of the rotation knob 24 relative to the handle 12 about axis T which is essentially the longitudinal center line of the handle. This is illustrated in FIG. 3 by the circular arrow R1. When the rotation knob 24 is rotated, in either direction, this causes a corresponding rotation of the instrument shaft 14. This is depicted in FIG. 3 by the rotational arrow R2. This same motion also causes a rotation of the end effector 16 about axis P as illustrated by the rotational arrow R3 in FIG. 3. In FIG. 3 the handle 12, via proximal bendable member 18, is shown tilted along axis T at an angle B1 to the instrument shaft longitudinal center axis. This tilting, deflecting or bending may be considered as in the plane of the paper. By means of the cabling this action causes a corresponding bend at the distal bendable member 20 to a position wherein the tip is directed along axis P and at an angle B2 to the instrument shaft longitudinal center axis. The proximal bendable member is controlled by virtue of its connection with the handle, so that movement of the handle causes control of the proximal bendable member and, in turn, the distal bendable member.

The combination of manipulation via the bendable members and rotation via the knob 24 provide a very precise and ergonomically comfortable degree of control for the surgeon. The instrument is adapted to be held in a number of different ways in use. In one technique, the instrument handle may be grasped so that the middle, ring and small fingers are about the surface 12c while the thumb engages the lever 22 and release button 96. The index finger may extend to engage the rotation knob 24. In this way all manipulations can be easily coordinated by the surgeon with one hand. The instrument may also be grasped in the following manner. The thumb may rest on the surface 12c while the fingers grasp the lever 22. The index finger may manipulate the knob 24. The thumb may also assist in manipulating the knob 24.

In the drawings a set of jaws is depicted, however, other tools or devices may be readily adapted for use with the instrument of the present invention. These include, but are not limited to, cameras, detectors, optics, scope, fluid delivery devices, syringes, etc. The tool may include a variety of articulated tools such as: jaws, scissors, graspers, needle holders, micro dissectors, staple appliers, tackers, suction irrigation tools and clip appliers. In addition, the tool may include a non-articulated tool such as: a cutting blade, probe, irrigator, catheter or suction orifice.

Reference is now made to FIGS. 4-8 for further details of the instrument 10 depicted in FIG. 1. In this particular embodiment the cabling within the instrument shaft is shown in a straight configuration such as illustrated in FIG. 5, and is shown in a bent condition in FIG. 6. The end effector or tool 16 is actuated by means of a jaw actuation means which is comprised primarily of the elongated lever 22 at the proximal end of the instrument. The lever 22 is supported from the housing at the lever pivot pin 23. Refer to FIGS. 4-6. The closing of the lever 22 against the handle 12 acts upon the slider 28 which is used to capture the very proximal end of the actuation cable 38. When the lever 22 is un-actuated (separated from the handle housing) this corresponds to the end effector jaws being in a fully open position. When the lever 22 closes this causes the slider 28 to move toward the right as depicted in FIG. 5, and then the jaws 44 and 46 are moved toward a closed position. In FIG. 5 the jaws are illustrated as closed so as to grasp, for example, a needle 45.

The instrument shaft 14 includes an outer shaft tube 32 that may be constructed of a light weight metal material or may be a plastic material. The shaft 32 may also be constructed to be inherently flexible, particularly for intraluminal use of the instrument. The proximal end of the tube 32 is received by the adaptor cover 26. The distal end of the tube 32 is secured to the distal bendable member 20. Refer to FIG. 6 for some further details of the distal bendable member 20. Within the outer shaft tube 32 there is provided a support tube 34 that is preferably constructed of a plastic material. Tube 34 extends between the distal bendable or flexible member 20 and the proximal bendable or flexible member 18. The jaw actuator cable 38 extends within this support tube 34. The support tube 34 may support along its length a plurality of spacers (not shown). Each of the spacers may be evenly spaced and provided with diametric guide slots for the cables.

Refer also now to FIGS. 5 and 6 for further details of the tool end of the instrument. The end effector 16 is comprised of a pair of jaws 44 and 46. As indicated previously these jaws may be used to grasp a needle 45 or other item. The upper jaw 44 fits within a channel in the lower jaw 46. A pivot pin 48 is used between the jaws to enable rotation therebetween. A translation pin 42 extends through slots of the jaws and engages with the jaw actuator cable 38. When the lever 22 is in its rest position the jaws are fully open. In that position the pin 42 is at a more distal location maintaining the jaw in an open position. As the cable 38 is pulled, then the pin 42 moves to the right in the slots, causing the jaws 44 and 46 to pivot toward a closed position as depicted in FIG. 5.

FIG. 5 also depicts a base wall 54 of the jaw 46. One end of the distal bendable member 20 is supported at this end wall 54. The member 20 may be secured to the wall 54 by an appropriate means. Adjacent to the base wall 54 there is provided an end disc 110a of the distal bendable member 20. Refer also to FIG. 11. The end disc 110a supports anchors for the flex control cables 100. FIG. 8 illustrates four such cables 100a, 100b, 100c and 100d.

The jaw actuator cable 38 terminates at its respective ends at the end effector and the rotation barrel 66 (see FIG. 5). Within each of the bendable sections or bendable members 18 and 20 there is provided a plastic tube. This includes a distal tube 60 and a proximal tube 62. Both of these tubes or sheaths may be constructed of a plastic such as polyethyletherkeytone (PEEK). The material of the tubes 60 and 62 is sufficiently rigid to retain the cable 38 and yet is flexible enough so that it can readily bend with the bending of the bendable members 18 and 20. The tubes have a sufficient strength to receive and guide the cable, yet are flexible enough so that they will not kink or distort, and thus keep the cable in a proper state for activation, and also defines a fixed length for the cable. The tubes 60 and 62 are longitudinally stiff, but laterally flexible.

The control of the end effector 16 is by means of the jaw actuator cable 38. As mentioned previously the very proximal end of the jaw actuator cable 38 is retained in the rotational barrel 66. As illustrated, for example, in FIG. 5 the cable 38 is secured to the rotational barrel 66. The rotational barrel 66 is supported within the slider 28. The slider 28 is also provided with a slot 74 that extends from the pocket and accommodates the link 70. The link 70 is the main means for actuating the slider 28 and, in turn, the actuator cable 38 from the lever 22.

The actuation link 70 is supported at one end from the lever 22 by means of the pivot pin 71. The opposite end of the link 70 is supported at another pin, referred to herein as slider pin 72. The pin 72 is retained for longitudinal movement in the slot 74 in the slider 28. FIG. 5 shows the respective pins 71 and 72 at the opposite ends of the link 70. FIG. 5 also illustrates the slider pin 72 urged against the actuator spring 76. The spring 76 is disposed within a compartment of the slider 28. The opposite end of the actuator spring 76 is retained by means of a retaining pin 80 that is disposed in the bore that accommodates the spring 76. FIG. 5 also shows the return spring 82 which is disposed within a bore in the handle for accommodating the spring 82. One end of the spring 82 is urged against an interior wall of the handle and the opposite end of the spring is urged against an end wall of the slider 28. The spring 76 is a preferably stronger spring than the spring 82 so that the spring 82 compresses first as the lever 22 is activated. Additional motion of the lever then causes the spring 76 to compress as the item is grasped. This dual spring arrangement prevents damage to the instrument cabling, particularly at the distal end of the instrument due to excessive forces imposed by the lever action.

The lever 22 actuates the end effector as it is pressed toward the handle body. The lever 22 operates with a ratchet and pawl arrangement with the lever capable of being depressed in ratcheted increments. This ratchet and pawl arrangement includes the ratchet 86 and pawl 88. To accommodate the ratchet 86, the slider 28 is provided with an end dish out or cut out. The pawl 88 is retained by the handle members 12a and 12b. In this regard in handle part 12a there may be a pocket for the pawl 88 and in the handle part 12b there may be provided a leg for retaining the pawl. The ratchet 88 pivots at the pivot pin 90 and is provided with a series of ratchet teeth that can hold the ratchet in successive positions corresponding to successive degrees of closure of the end effector. A torsion spring 92 is disposed partially about the pivot 90 and urges the ratchet teeth into contact with the pawl 88.

The ratchet and pawl arrangement also includes an integral release means that is usually engageable by the surgeon's thumb. As depicted in FIG. 5, on one side of the pivot 90 there is the pawl 86 and on the other side of the pivot there is the arm 94. A release button 96 is formed at the base of the arm 94. When a force is directed against the button 96 in the direction of arrow M in FIG. 5 then this releases the ratchet and pawl arrangement and returns the lever 22 to its released position with the jaws fully opened. The pressing of the button 96 rotates the ratchet 86 out of engagement with the pawl 88.

Reference is now made to the cabling that extends between the proximal and distal bendable members. This cabling is provided so that any bending at the proximal bendable member is converted into a corresponding bending at the distal bendable member. The proximal bending causes the cabling on one side to tension and on the opposite side to relax. The bendable members that are described herein enable bending in all directions. In the preferred embodiment described herein, the distal bendable member is approximately ½ the diameter of the proximal bendable member as illustrated in FIG. 35. However, as indicated before other diameter relationships can be used depending upon the particular use of the instrument and the medical procedure in which it is being used.

The control between the proximal bendable member 18 and the distal flexible member 20 is carried out by means of the flex control cables 100. There are four such cables in the illustrated embodiment identified, for example, in FIG. 8 as cables 100a, 100b, 100c and 100d. At the distal end of these cables, as has been described hereinbefore, the cables connect to the anchors at the most distal disc 110. Cables 100 are retained at their proximal ends by cable end lugs 102. Four springs 104 are retained between these end lugs 102 and a wall of the hub 101. Refer to FIG. 5 for an illustration of the end lugs 102 and the springs 104. The springs 104 tension or take up the slack on the cables. Between the bendable members, the cables 100 may be guided by means of the slots in spacers (not shown) that may be disposed along the support tube 34. Within the adaptor cover 26, the cables 100 extend through the transition member 106. The cables then extend to a larger outer diameter locus as they extend through the proximal bendable member as depicted in FIGS. 5 and 6. The stepped transition member 106 may be of metal and is disposed adjacent to the end of tube 34.

FIGS. 5 and 6 depict the distal end of the instrument and, in particular, the distal flexible member 20. This is in the form of an interlocking disc arrangement comprised of a series of discs or disc elements 110 that are of semi-spherical configuration and that are adapted to nest with each other and to inter-engage from one to the next. See also FIG. 11. Each of these discs have holes for receiving the actuating cables 100 that are positioned at 90 degree intervals corresponding to the desired position of the cables. These discs also include opposite end discs 110a and 110b. FIG. 6 shows the cables 100 passing through the end disc 110b. The other end disc 100a supports the cable ends at anchors. A bearing 112 is disposed between the base wall 54 of the end effector 16 and the end disc 110a. This bearing enables the end effector 16 to readily rotate relative to the discs 110. A second bearing 114 is also provided at the end disc 110b to enable rotation between the end disc 110b and the outer tube 32. Thus, the inner tube 60, cables 100 and discs 110 are non-rotational while the outer tube 32, along with the end effector are rotational from the rotation knob 24. The distal bendable member 20 receives the aforementioned PEEK tube 60 which extends through a center hole in each disc, similar to that shown in FIG. 7 for the proximal bendable member.

The distal motion member 20 also includes an outer bellows 116 that is attached at opposite ends to the outer tube 32 and the base wall 54. A sleeve 117 may be used to attach the bellows 116 to the tube 32. A similar sleeve 118 may be used to attach the opposite end of the bellows 116 to the base wall 54. Refer also to FIG. 11. Any rotation imparted to the outer instrument shaft 32 is coupled via the bellows 116 to the end effector 16. Thus, there is an inner instrument section that is maintained stationary during instrument rotation and that includes the inner discs, cables and inner sleeves. At the same time there is an outer instrument section that is capable of rotation relative to the inner instrument section and that includes the outer sleeve, bellows and end effector.

The proximal motion member 18 is constructed in a similar manner to the distal motion member and includes a series of discs 120 that are of semi-spherical configuration and that are adapted to nest with each other and to inter-engage from one to the next. Each of these discs have holes for receiving the actuating cables 100 that are positioned at 90 degree intervals corresponding to the desired position of the cables. These discs also include opposite end discs 120a and 120b. FIGS. 6 and 7 show the cables 100 passing through the end disc 120a. The other end disc 120b engages the hub 101 which is secured within the handle 12. A bearing or bushing 122 is disposed between the hub 101 and the rotation knob 24. This bearing 122 enables the rotation knob 24 to readily rotate relative to the hub 101. A second bearing or bushing 124 is also provided at the adaptor 26 to enable rotation between the transition member 106 and the adaptor 26. The inner tube 62, cables 100 and discs 120 are non-rotational while the outer tube 32, along with the adaptor are rotational from the rotation knob 24. Cables 100 are retained at their proximal ends by cable end lugs 102. Four springs 104 are retained between these end lugs 102 and a wall of the hub 101. Refer to FIGS. 6 and 7 for an illustration of the end lugs 102 and the springs 104. The springs 104 tension or take up the slack on the cables. The distal bendable member 18 receives the aforementioned PEEK tube 62 which extends through a center hole in each disc.

The proximal motion member 18 also includes an outer bellows 126 that is attached at opposite ends to the adaptor 26 and the rotation knob 24. A sleeve 127 may be used to attach the bellows 126 to the adaptor 26. A similar sleeve 128 may be used to attach the opposite end of the bellows 126 to the rotation knob 24. Any rotation imparted to the rotation knob 24 is coupled via the bellows 126 to the adaptor and instrument shaft, and from there to the distal end of the instrument to rotate the end effector. Thus, there is a proximal inner instrument section that is maintained stationary during instrument rotation and that includes the inner discs, cables and inner sleeves. At the same time there is an outer instrument section that is capable of rotation relative to the inner instrument section and that includes the outer sleeve, bellows and rotation knob.

The embodiment described in FIGS. 4-8 also includes a lock feature that enables the position between the proximal and distal motion members to be fixed in a desired position, such as the position illustrated in FIG. 6 where the handle has been bent downwardly causing a corresponding bending of the tool upwardly. In FIG. 6 the top cable is in tension and the bottom cable in relaxation. Once the surgeon has the instrument in the desired bent position then a locking member is used to conveniently hold the instrument in that position. The locking member is shown in FIGS. 5 and 6 as the lock lever 140 that is pivotally supported from the handle by means of the pivot pin 142. See also the locking lever 140 in FIGS. 1-3. FIG. 5 shows the lock lever 140 in its released position in which the bendable members are permitted to bend in the normal operation of the instrument without being locked.

This locking feature is an important adjunct to the other controls of the instrument enabling the surgeon to lock the instrument once in the desired position. This makes it easier for the surgeon to thereafter perform surgical procedures without having to, at the same time, hold the instrument in a particular bent configuration. The relatively rotatable inner and outer instrument sections also enable the surgeon, in the locked state, to use the rotation knob to control the end effector to rotate about the distal end effector longitudinal axis. Also, having the locking lever or similar locking mechanism directly at the handle within reach of the user's hand provides an effective and convenient way of controlling the instrument tool with one hand.

Thus, the control at the handle is used to bend the instrument at the proximal bendable member to, in turn, control the positioning of the distal bendable member and tool. The "position" of the tool is determined primarily by this bending action and may be considered as the coordinate location at the distal end of the distal bendable member. This positioning is in three dimensions. The "orientation" of the tool, on the other hand, relates to the rotational positioning of the tool about the illustrated distal tip axis (see axis P in FIG. 3).

The present invention actually describes a number of different embodiments of the locking member. In a first embodiment the locking member 140, as illustrated in FIGS. 4-8, locks the position of the instrument by locking the proximal bendable member. Once the proximal bendable member is locked, then this maintains the cable positions in a fixed position and thus also maintains a locked position for the distal bendable member. In another embodiment as described in FIG. 9 and described in further detail hereinafter, the locking member locks the distal bendable member rather than the proximal bendable member. However, in this embodiment the locking of the distal bendable member also maintains the proximal bendable member in a fixed position. In still another embodiment of the invention such as illustrated in FIG. 10, separate locking members are provided, one for locking the proximal bendable member and the other for locking the distal bendable member so that both bendable members are affirmatively and separately locked.

In the embodiment of FIGS. 4-8, the locking lever 140 is provided with a detent arrangement that enables it to be normally maintained in an unlocked position such as the one illustrated in FIG. 5. The detent arrangement that is referred to includes a projection 144 on the locking lever 140 and a depression 145 in the handle. The locking lever 140 is biased to the position illustrated in FIG. 5 by means of a spring 146. A locking cable 150 extends about a pulley 152 and is secured at one end with the spring 146. The opposite end of the cable 150 terminates at 154 at a distal surface of the end disc 120a. In a position illustrated in FIG. 5, the cable 150 is relaxed and thus there is no force imposed upon the end disc 120a to lock it with the other discs. Accordingly, in the position of the locking lever 140 in FIG. 5, the proximal bendable member is free to bend and deflect controlling the distal bendable member.

The locking of the proximal bendable member is illustrated in FIG. 6 wherein the locking lever 140 has now been moved in the direction of arrow 141 to pivot the lever about pin 142 and engage the protuberance 144 on the lever 140 with the depression 145 in the handle. This action maintains the locking lever 140 in the position illustrated in FIG. 6. This action pulls the cable 150 thus providing a clamping force at the end disc 120*a*. This clamping force is illustrated by the arrow 155 in FIG. 6. This clamping action forces the end disc 120*a* in the direction of arrow 155 against all of the other successive discs 120 that comprise the proximal bendable member. This action firmly locks the bend at the particular position of the proximal bendable member as occurs when the locking lever is depressed. With the proximal bendable member locked in a particular position, this also maintains the distal bendable member in its corresponding position such as the bent position illustrated in FIG. 6. Once the proximal bendable member is locked that hold the distal bendable member in the corresponding same position as the bend control cables are of the same length, and once the proximal bendable member is frozen in a particular position this retains the distal bendable member in its corresponding fixed position.

Figure 7B:
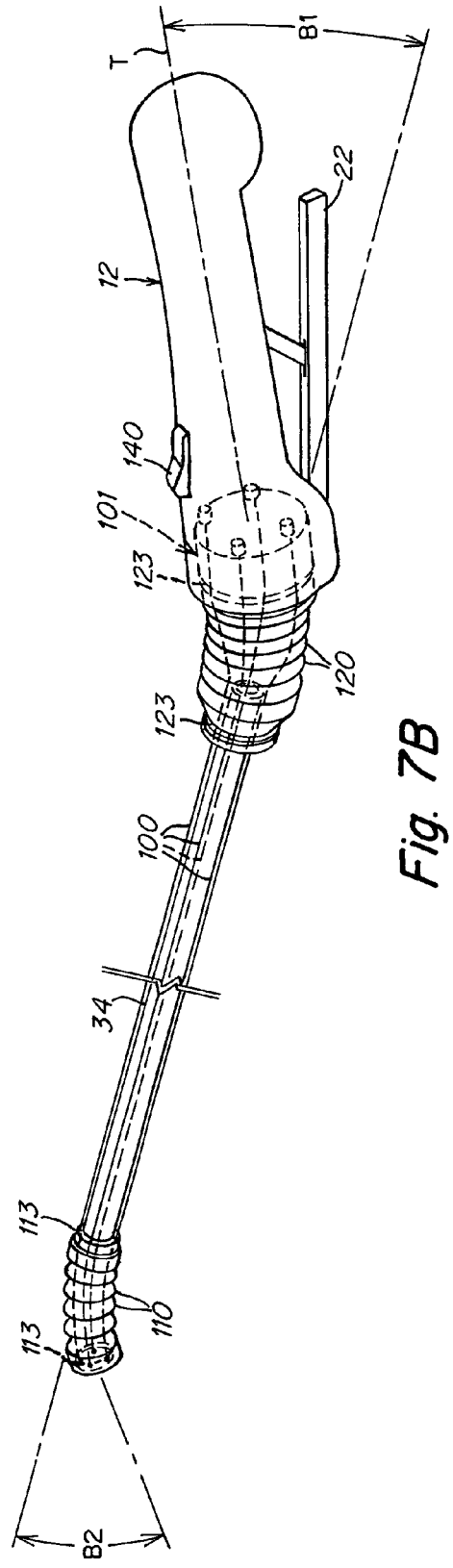

Refer also to FIGS. 7A and 7B for a further explanation of the operation of the instrument described in FIGS. 4-8. FIG. 7A shows only the outer instrument section while FIG. 7B separately shows the inner instrument section. The outer instrument section may also be referred to as an outer sheath assembly while the inner instrument section may also be referred to as an inner armature assembly. The outer sheath assembly provides for end effector rotation via the rotation knob 24 and also provides bending or flexing in three dimensions or axes via the proximal and distal bellows. The inner armature assembly provides the bending action between the discs 110 and 120 via cabling from the handle 12. The outer sheath assembly in FIG. 7A includes, from proximal to distal end of the instrument, the rotation knob 24, bellows 126, outer tube 32, bellows 116 and tool 16. The inner armature assembly in FIG. 7B includes, from proximal to distal ends of the instrument, handle 12, proximal bendable discs 120, inner tube 34 and distal bendable discs 110. FIG. 7A also illustrates the position of the proximal bearings 122, 124 and the distal bearings 112, 114. FIG. 7B illustrates the location of the corresponding bearing seats at 113 and 123.

FIG. 7A also depicts the rolling motion that can be carried out with the instrument of the present invention. This can occur by virtue of the rotation of the rotation knob 24 relative to the handle 12 about axis T which is essentially the longitudinal center line of the handle. This is illustrated in FIG. 7A by the circular arrow R1. When the rotation knob 24 is rotated, in either direction, this causes a corresponding rotation of the instrument shaft which is depicted in FIG. 7A by the rotational arrow R2. This same motion also causes a rotation of the end effector 16 about axis P as illustrated by the rotational arrow R3 in FIG. 7A. In FIG. 7B the handle 12, via the proximal bendable member, is shown tilted along axis T at an angle B1 to the instrument shaft longitudinal center axis causing a tilting at angle B2 at the distal end of the instrument.

Reference is now made to FIG. 9 for an alternate embodiment of the invention in which the locking member locks the distal bendable member rather than the proximal bendable member. FIG. 9 is a longitudinal side elevation view of a surgical instrument employing such a locking member identified in FIG. 9 as locking lever 240. In FIG. 9 the same reference characters are used to identify parts of the instrument that are substantially the same as the parts of the instrument illustrated in FIGS. 4-8. Thus, the instrument of FIG. 9 comprises a handle 12, a lever 22, a rotation knob 24, and a proximal bendable member 18 connected to a distal bendable member 20 by way of the instrument shaft 14. An end effector 16 is supported at the very distal end of the instrument.

The primary difference between the embodiment illustrated in FIG. 9 and the previous embodiment illustrated in FIGS. 4-8 is that the locking member 240 actuates a cable 250 that is coupled to the very distal end of the instrument for locking the distal bendable member 20 rather than the proximal bendable member. The locking lever 240 may be identical to that described in FIGS. 5 and 6 and includes a detent and spring arrangement for enabling the opposite position pivoting of the lever member 240. FIG. 9 also illustrates the very distal end of the cable 250 at end 254. When the lever member 240 is pivoted in the direction of arrow 242 this pulls the cable 250 to the right in FIG. 9 and a pulling force is exerted at the distal end of the instrument, as indicated by the arrow 255 in FIG. 9. This causes the most distal disc member 110*a* to firmly engage with the other successive disc members locking the distal bendable member in a predetermined position. With the distal bendable member locked in a particular position, this also maintains the proximal bendable member in its corresponding position such as a bent position like that illustrated in FIG. 6. The distal bendable member is locked in the particular position that it is disposed at when the locking lever is actuated.

Reference is now made to FIG. 10 for still a further embodiment of the present invention in which a pair of locking members is employed. These are identified in FIG. 10 as locking levers 140 and 240. FIG. 10 is a longitudinal cross-sectional view showing the instrument in a bent position where the proximal bendable member has been deflected through the angle B1 causing a like deflection of the distal end of the instrument at the end effector through an angle B2.

In the embodiment of FIGS. 10 and 11, there are thus two separate locking levers that can be operated each individually or they can be operated in tandem. The locking lever 140 controls the cable 150 which in turn controls the locking of the proximal bendable member at point 154. The locking lever 240 controls the cable 250 which extends to the distal end of the instrument and controls the locking of the distal bendable member 20 at point 254. In FIG. 10 the locking lever 240 is shown locked while the locking lever 140 is shown unlocked.

In FIG. 10 the two locking levers are described as providing separate control of the locking of the respective proximal and distal members. As such, the individual locking levers only control their respective bendable members. In an alternate embodiment the locking levers 140, 240 may be formed as one single lever for controlling both of the cables 150, 250 at the same time. Thus, when the single locking lever is actuated that locks both the proximal and distal bendable members.

FIG. 11 is a cross-sectional view at the distal end of the instrument showing somewhat further details in an enlarged cross-section. This illustrates the cable 250 that extends to the end disc 110*a* and which may be pulled to urge the most distal end disc 110*a* against the adjacent discs 110. This action at point 254, in turn, causes each of the discs that comprise the distal bendable member to inter-engage thus locking the distal bendable member in a particular bent state. FIG. 11 also shows the control cables 100 and the tool actuation cable 38.

The control between the proximal bendable member 18 and the distal flexible member 20 is carried out by means of the flex control cables 100. There are four such cables in the illustrated embodiment identified, for example, in FIG. 8 as cables 100*a*, 100*b*, 100*c* and 100*d*. At the distal end of these cables, as has been described hereinbefore, the cables connect to the anchors at the most distal disc 110. Cables 100 are retained at their proximal ends by cable end lugs 102. Four springs 104 are retained between these end lugs 102 and a wall of the hub 101. Refer to FIG. 5 for an illustration of the end lugs 102 and the springs 104. The springs 104 tension or take up the slack on the cables. Between the bendable members, the cables 100 may be guided by means of the slots in spacers (not shown) that may be disposed along the support tube 34. Within the adaptor cover 26, the cables 100 extend through the transition member 106. The cables then extend to a larger outer diameter locus as they extend through the proximal bendable member as depicted in FIGS. 5 and 6. The stepped transition member 106 may be of metal and is disposed adjacent to the end of tube 34.

Reference is now made to a further embodiment of the present invention illustrated in FIGS. 12-15. In the previous embodiments described herein, the bend control cables 100 were non-rotatable and formed part of the inner instrument section. In the embodiment illustrated in FIGS. 12-15, the control cables 200 are positioned through the bellows at both the proximal and distal ends of the instrument and are adapted to rotate upon rotation of the rotation knob 24, the instrument shaft 14 and the end effector 16. In the embodiment of FIGS. 12-15 there may be provided two locking levers 140 and 240 for respectively controlling the cables 150 and 250. The cable 150 controls the locking of the proximal bendable member while the cable 250 controls the locking of the distal bendable member.

FIG. 12 depicts the distal end of the instrument and, in particular, the distal flexible member and end effector. This is in the form of an interlocking disc arrangement comprised of a series of discs or disc elements 210 that are of semi-spherical configuration and that are adapted to inter-engage from one to the next. The discs 210 in FIG. 12 are of somewhat different construction than the discs shown before in FIG. 11. Each of these discs have a tapered center passage for receiving the inner sleeve 260 and the actuation cable 38 which extends in the sleeve 260. These distal discs 210 also include opposite end discs 210a and 210b. FIG. 12 shows the cables 200 passing through holes in the outer bellows 216 rather than through the discs. This somewhat simplifies the disc construction for this embodiment.

One end disc 210a is supported adjacent to the end wall 54 and the other end disc 210b is supported adjacent the collar 211. A bearing or bushing 212 is disposed between the base wall 54 of the end effector 16 and the end disc 210a. This bearing 212 enables the end effector 16 to readily rotate relative to the discs 210. A second bearing or bushing 214 is also provided at the end disc 210b to enable rotation between the collar 211 and the outer tube 32. Thus, the inner tube 260 and discs 210 are non-rotational while the outer tube 32, along with the cables, bellows and end effector are rotational from the rotation knob 24. The distal bendable member 20 receives the aforementioned PEEK tube 260 which extends through a center hole in each disc.

The distal motion member 20 has the outer bellows 216 attached at opposite ends to the outer tube 32 and the base wall 54. A sleeve 217 may be used to attach the bellows 216 to the tube 32. A similar sleeve 218 may be used to attach the opposite end of the bellows 216 to the base wall 54. Any rotation imparted to the outer instrument shaft 32 is coupled via the bellows 216 to the end effector 16. Thus, there is an inner instrument section that is maintained stationary during instrument rotation and that includes the inner discs and inner sleeves. At the same time there is an outer instrument section that is capable of rotation relative to the inner instrument section and that includes the outer sleeve, bellows, cabling and end effector.

Figure 13:
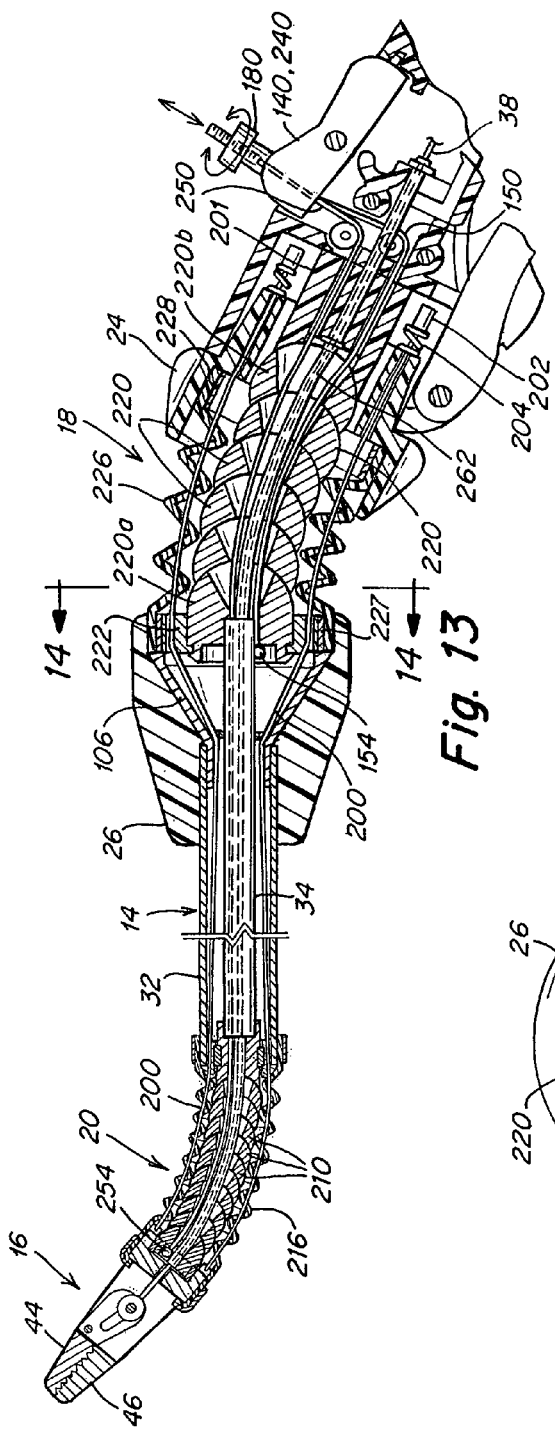
FIG. 13 is a fragmentary cross-sectional view of the embodiment of FIG. 12 with the instrument in a bent condition and locked.

The proximal motion member is constructed in a similar manner to the distal motion member and includes a series of discs 220 that are of semi-spherical configuration and that are adapted to inter-engage from one to the next. Each of these discs has a main tapered center hole for receiving the tool actuator cable 38 and tube 262. The tapers in both proximal and distal discs enable the bending without interfering with the cabling and tubes that extend therethrough. These discs also include opposite end discs 220a and 220b. FIG. 13 shows the cables 200 passing through the bellows 226. The end disc 220b engages the hub 201 which is secured within the handle 12. A bearing or bushing 222 is disposed between the disc 220a and the adaptor 26. This bearing 222 enables the adaptor 26 to readily rotate relative to the disc 220a. The inner tube 262 and discs 220 are non-rotational while the outer tube 32, along with the adaptor and bellows are rotational from the rotation knob 24. Cables 200 are retained at their proximal ends by cable end lugs 202. Four springs 204 are retained between these end lugs 202 and a wall of the hub 201. The springs 204 tension or take up the slack on the cables. The distal bendable member receives the aforementioned PEEK tube 262 which extends through a center hole in each disc.

The proximal motion member has the outer bellows 226 attached at opposite ends to the adaptor 26 and the rotation knob 24. A sleeve 227 may be used to attach the bellows 226 to the adaptor 26. A similar sleeve 228 may be used to attach the opposite end of the bellows 226 to the rotation knob 24. Any rotation imparted to the rotation knob 24 is coupled via the bellows 226 to the adaptor and instrument shaft, and from there to the distal end of the instrument to rotate the end effector. Thus, there is a proximal inner instrument section that is maintained stationary during instrument rotation and that includes the inner discs and inner sleeve. At the same time there is an outer instrument section that is capable of rotation relative to the inner instrument section and that includes the outer sleeve, bellows, cables and rotation knob.

In all the embodiments that use a bellows, such as the bellows 126 in FIG. 6 or the bellows 226 in FIG. 13, it is noted that the bellows itself functions as a torque transmission means whether cabling passes therethrough or not. In other words the bellows have a sufficient rigidity thereto so as to be able to transmit the rotational motion from the rotation knob to the instrument shaft. This may be referred to as the bellows providing rotational torque to distal members such as the instrument shaft and end effector. At the same time the bellows is constructed and arranged to be sufficiently flexible so as to flex (compress or expand) as the bending action is performed. Refer, for example, to FIG. 6 where the bellows 126 is shown flexed to a more open position on the top while flexed to a more closed position at the bottom. Other foldable members may also be used as an alternative to a bellows.

The embodiment described in FIGS. 12-15 also includes a lock feature that enables the relative position between the proximal and distal motion members to be fixed in a particular position, such as the position illustrated in FIG. 13 where the handle has been bent downwardly causing a corresponding bending of the tool upwardly. Once the surgeon has the instrument in the desired bent position then a locking member is used to hold the instrument in that position. The locking member is shown in FIG. 13 as the locking levers 140, 240 that are pivotally supported from the handle by means of one or separate pivot pins. FIG. 13 shows the lock lever in its engaged position in which the bendable members are locked in a predetermined position. This locking feature is an important adjunct to the other controls of the instrument enabling the surgeon to lock the instrument once in the desired position. This makes it easier for the surgeon to thereafter perform surgical procedures without having to, at the same time, hold the instrument in a particular bent configuration. Instrument rotation is capable even in the locked state.

Figure 15:
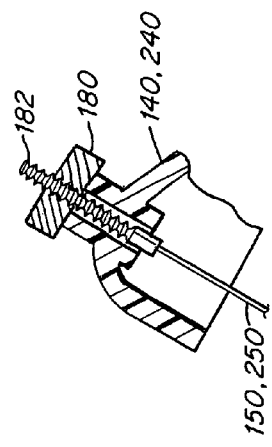
FIG. 15 is a fragmentary cross-sectional view of the tension adjustment member used in the embodiment of FIG. 13.
Figure 14:
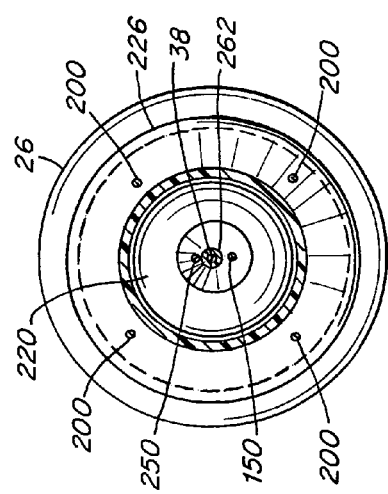
FIG. 14 is a cross-sectional view taken along line 14-14 of FIG. 13.

FIGS. 13-15 also illustrate the lock cables 150 and 250 that are controlled respectively from the lock levers 140 and 240.

The cable 150 terminates at node or point 154 where the termination ends at the disc 220a. Pulling on the cable 150 causes the discs 220 to be tightly engaged holding the bendable section in a particular configuration such as shown in FIG. 13. Similarly, the cable 250 terminates at node or point 254 at the distal end of the instrument where the termination ends at the disc 210a. Pulling on the cable 250 causes the discs 210 to be tightly engaged holding the bendable section in a particular configuration such as shown in FIG. 13. In the embodiment described in FIGS. 12-15 the locking levers 140, 240 are adjustable by means of the turnbuckle arrangement shown in an enlarged fragmentary view in FIG. 15. This arrangement includes a rotation wheel 180 positioned on the lever and having an internal threaded passage for receiving the threaded end 182 of the lock control cable. The wheel 180 can be rotated to adjust the level of tension imposed on the control cable. In both the proximal and distal discs by pulling on the most distal disc this causes pressure to be applied to all more proximal discs keeping their bendable member in a particular curvature, such as shown in FIG. 13.

In the embodiments of the present invention illustrated previously in FIGS. 1-15, the locking member has been in the form of a pivotal lever. However, various other types of locking members may be employed. These locking members are preferably mounted on the handle or close to the handle so that they are in easy reach of the user of the instrument. The locking member is also preferably manually controllable so as to be in either a released position or an activated position. Reference is now made to FIG. 16 for an alternate embodiment of a locking means in the form of a slide switch 270 that is appropriately mounted in the handle 12. The slide switch 270 retains the proximal end of the control cable 151. The control cable 151 is illustrated in FIG. 16 as passing over a pair of pulleys 152 and 153. Of course, the distal end of the control cable 151 can couple to either the proximal or distal bendable member. Also, in another alternate embodiment a pair of such slide switches 270 may be provided for controlling respective proximal end distal bendable members.

In FIG. 16 the slide button 270 is illustrated as supported in the handle 12 in an opening 274. The locking mechanism is also provided with a ratchet surface 272 for engagement with a like ratchet surface on the slide switch 270 so as to provide selective incremental positioning of the slide switch 270. In FIG. 16 the slide switch 270 is shown in its released position and would be moved to the right in the opening 274 to move toward its locked position. A leaf spring 275 is supported in the slide switch 270. The leaf spring 275 urges the teeth into engagement. Pushing down on the switch 270 in the direction of arrow 276 releases the engagement between the teeth so that the slide switch can be moved to its release position.

In the previous embodiments described herein, a separate cable or cables have been provided to provide the locking function of the instrument. A proximal bendable member locking cable has been employed and/or a distal bendable member locking cable. Thus, the bending control cables 100, 200 in these embodiments have been devoted to only the bending function. An alternate embodiment of the invention is illustrated in FIGS. 17 and 18 in which the bend control cables function, not only for the bending action, but also for the locking function. This is carried out by virtue of pulling all cables in unison to perform the locking function. At the same time, during locking, the rotation function is operable through the rotation knob 24.

In the embodiment of FIGS. 17 and 18 the same reference characters are used to identify similar parts of the instrument as found in the earlier embodiment described in FIGS. 4-8. In this embodiment the instrument comprises a handle 12, a proximal bendable member 18, an instrument shaft 14, a distal bendable member 20 and an end effector 16. As in the embodiment illustrated in FIG. 6, in FIG. 17 there is also provided a rotation knob 24 rotatable relative to the hub 101 mounted within the handle housing. This instrument also has the aforementioned inner and outer instrument sections that enable relative rotation therebetween.

FIG. 17 also illustrates the four cables 100 that are used to control the deflection of the bendable members. In the embodiment of FIG. 6 these cables were secured within the hub 101. In the embodiment of FIG. 17 the proximal end of these cables are secured instead to a carriage 165 that can be moved between released and locked positions. The locking occurs by means of pulling on all four cables 100 at the same time so as to freeze or fix the instrument in a particular bent position. By pulling longitudinally on the cables there is a force imposed illustrated by the arrows 170 in FIG. 17 that causes the discs of the distal bendable member to lock, one to the next. This action also correspondingly freezes the position of the proximal bendable member.

In the embodiment of FIGS. 17 and 18 the locking member comprises a pivotal locking lever that may have a detent arrangement associated therewith similar to that disclosed in FIG. 6. The lever 160 is pivoted at pivot pin 171. A linkage 161 couples from the lever 160 to a slider 163. The slider 163 has a wedge or tapered shape as illustrated in the cross-sectional view of FIG. 17 and, at one side, bears against a proximal end 164 of the carriage 165. The carriage 165 is adapted to translate in a journal 169 provided in the handle housing. A wedge shaped boss 175 is provided on the handle. The distal end of the carriage 165 is in the form of a plate that supports the four cables 100. Each of the cables has associated therewith an end lug 167 and a spring or resilient pad 168. The carriage is also provided with opposed pins 177 that constrain the carriage movement by moving in associated handle slots.

In the position illustrated in FIG. 17, the carriage 165 may be considered as at its released or normal position. This permits the bending action to occur between the proximal and distal bendable members without any locking. When the locking lever 160 is moved in the direction of arrow 173, then the slider 163 bears against the end 164 and boss 175, thus causing the carriage 165 to translate toward the right as viewed in FIG. 17. This action pulls all of the cables 100 toward the right thus imposing the force at the distal end of the instrument as illustrated by the arrows 170. This compresses together both proximal and distal disc members in the predetermined and pre-selected position that the user has assumed.

Another aspect of the surgical instrument of the present invention is the ability to adapt the instrument to a wide variety of medical procedure. This includes, but is not limited to, access to a body cavity such as through an incision or intraluminal use such as through a natural body aperture to a body lumen. The introduction of the surgical instrument into the anatomy may also be by percutaneous or surgical access to a lumen, cavity or vessel, or by introduction through a natural orifice in the anatomy.

There are several improvements brought forth by employing bendable sections for the motion members particularly as opposed to other mechanisms such as pivotal joints or ball-and-socket joints.

A first important attribute of a bendable member is in its inherent lateral (bending) stiffness, especially when used for the proximal handle motion member. In a jointed arrangement the proximal joint is situated between the elongated shaft and the control handle, together with the fulcrum at the incision. This behaves as a "double-joint" and the instrument may have a serious tool stability issue if the joint is "free" to move. Suppose the operating surgeon slightly moves his/her wrist while holding the control handle of the instrument. If the joint is "free" to move without providing substantial support resistance, due to the fulcrum effect of the long elongated shaft passing through the incision, it will result in substantial, unintended swinging of the tool end of the instrument in opposite direction. In a typical laparoscopic or endoscopic procedure where the operating field is small, such instability of the tool will render the tool potentially dangerous and unusable. Unlike the pivotal or ball-and-socket joints that are "free" to move, a bendable member has inherent stiffness which acts to provide necessary support for stabilizing the operator hand's wrist movement, which in turn stabilizes the tool motion. By varying the material and geometry of the bendable member, the appropriate level of stability could be selected.

A second important attribute of the bendable member, especially for bending in two degrees of freedom, is its uniformity in bending. Because the bendable member can bend in any direction uniformly, it has no inherent singularity, and as the result, the operator can produce uniform rolling motion of the tool, an important motion for tasks such as suturing, simply by rolling the control handle. On the other hand, if the motion members are comprised of series of pivotal joints, not only may it bind due to singularities, but the rolling of the control handle will result in unwanted side motion of the tool as well, affecting its usability for surgical procedure.

A third attribute of the bendable member is its ability to transmit substantial torque axially. By selecting appropriate material and geometry, the bendable member can be constructed to transmit torque axially necessary to perform surgical procedure. On the other hand, the motion member comprised of ball-and-socket joints will not be able to transmit the necessary torque from the handle to the tool end.

A fourth attribute of the bendable member is that it has no sharp bending point, location or pivot and thus this results in an increased life and higher performance. Either pivotal or ball-and-socket joints on the other hand have sharp corners which can increase friction, reduce life and decrease performance of the tool actuation push rod passing through.

A fifth attribute of the bendable member is in the reduction of manufacturing cost. The bendable motion member can be injection molded as a single body, thus significantly reducing the cost. Pivotal or ball-and-socket joints are comprised of more parts, and this results in a higher manufacturing cost.

Lastly, a sixth attribute of the bendable member is that it can be easily customized. By varying the stiffness at different points of the bendable member, one can optimize its bending shape for specific applications.

While this invention has been particularly shown and described with references to preferred embodiments thereof, it will be understood by those skilled in the art that various changes in form and details may be made therein without departing from the scope of the invention encompassed by the appended claims. For example, the embodiments described herein have primarily used four control cables for providing all direction motion of the motion members. In alternate embodiments fewer or greater numbers of cables may be provided. In a most simplified version only two cables are used to provide single DOF action at the bendable motion member. Also, the disclosed embodiment uses a handle that is essentially in line with the instrument shaft. In an alternate embodiment of the invention the handle can be off axis or at an angle to the instrument shaft in the rest position of the instrument. In the illustrated embodiments a rotation knob has been used to perform the function of rotating the distal instrument tip. In an alternate embodiment of the invention other means may be provided to accomplish such tip rotation. For example, a slide member may be used in place of a rotation knob, or any other moveable member that controls the instrument shaft and instrument tip for rotation of the end effector about a distal tool axis such as shown in FIG. 3 (axis P).

What is claimed is:

1. A surgical instrument comprising:
an instrument shall having proximal and distal ends;
a tool disposed from the distal end of the instrument shaft;
a control handle coupled from the proximal end of the instrument shaft and having a proximal end where the control handle is grasped and a distal end;
a distal motion member for coupling the distal end of said instrument shaft to said tool;
a proximal motion member for coupling the proximal end of said instrument shall to said control handle;
actuation cabling extending between said distal and proximal motion members for coupling motion of said proximal motion member to said distal motion member for controlling the positioning of said tool;
said proximal motion member including at least one partially spherical element;
said control handle having formed at the distal end thereof a partially spherical formed socket for receiving the at least one partially spherical element;
a locking mechanism for fixing the position of the said proximal motion member at a selected position and having locked and unlocked states;
said locking mechanism including a locking lever that is mounted at the control handle and movable relative to the control handle, and a slideable locking piece responsive to the manual operation of the locking lever and terminated at the proximal motion member for selectively locking a bent position of the proximal motion member to, in turn, maintain via said actuation cabling a corresponding bent position of the distal motion member;
a tool actuation lever mounted at the control handle for actuating the tool and a tool actuation cable that connects the tool actuation lever to the tool;
a rotation knob mounted at the control handle and rotated relative to the control handle for controlling the tool to rotate about a distal tool axis so as to control the orientation of the tool;
said rotation knob mounted at the control handle and disposed at a location that is proximally of at least a part of the proximal motion member;
a torque transmission member coupled with and extending distally from the rotation knob for controlling the orientation of the tool;
said locking lever mounted at the control handle at a position that is between the proximal motion member and at least part of the tool actuation lever;
said rotation knob further mounted at the control handle at a location that is adjacent to the locking lever;
whereby, when the locking lever is moved to the locked state, the locking piece is slid linearly causing the partially spherical element of the proximal motion member to lockingly engage the partially spherical formed socket to thus hold the proximal motion member in the selected fixed position.

2. The surgical instrument of claim 1 wherein said locking lever is mounted at the control handle at a location that is spaced proximally from the proximal motion member.

3. The surgical instrument of claim 1 wherein the rotation knob is located between the tool actuation lever and at least a part of the proximal motion member.

4. The surgical instrument of claim 1 wherein the tool actuation lever includes a manual engagement section and a pivot for the tool actuation lever from the control handle.

5. The surgical instrument of claim 4 wherein the rotation knob and locking lever are both disposed closer to the distal end of the control handle than at least part of the manual engagement section of the tool actuation lever.

6. The surgical instrument of claim 4 wherein the rotation knob and locking lever are both disposed distally relative to the manual engagement section of the tool actuation lever.

7. The surgical instrument of claim 1 wherein said torque transmission member is disposed separate from and concentric with said proximal motion member.

8. The surgical instrument of claim 1 wherein the rotation knob and torque transmission member are separate from and independently operable from the proximal and distal motion members.

9. The surgical instrument of claim 1 wherein the slideable locking piece is disposed substantially along a central axis of the proximal motion member, and the torque transmission member has a length commensurate with the distance between the rotation knob and tool.

10. A surgical instrument comprising:
an instrument shaft having proximal and distal ends;
a tool disposed from the distal end of the instrument shaft;
a control handle coupled from the proximal end of the instrument shaft and having a proximal end where the control handle is grasped and a distal end;
a distal motion member for coupling the distal end of said instrument shaft to said tool;
a proximal motion member for coupling the proximal end of said instrument shaft to said control handle;
actuation cabling extending between said distal and proximal motion members for coupling motion of said proximal motion member to said distal motion member for controlling the positioning of said tool;
said proximal motion member including at least one partially spherical element;
said control handle having formed at the distal end thereof a partially spherical formed socket for receiving the at least one partially spherical element;
a locking mechanism for fixing the position of the said proximal motion member at a selected position and having locked and unlocked states;
said locking mechanism including a locking lever that is mounted at the control handle and movable relative to the control handle, and a slideable locking piece responsive to the manual operation of the locking lever and terminated at the proximal motion member for selectively locking a bent position of the proximal motion member to, in turn, maintain via said actuation cabling a corresponding bent position of the distal motion member;
a tool actuation lever mounted at the control handle for actuating the tool and a tool actuation cable that connects the tool actuation lever to the tool;
a rotation knob mounted at the control handle and rotated relative to the control handle for controlling the tool to rotate about a distal tool axis so as to control the orientation of the tool;
said rotation knob mounted at the control handle and disposed between the tool actuation lever and at least a part of the proximal motion member;
a torque transmission member coupled with and extending distally from the rotation knob for controlling the orientation of the tool;
said tool actuation lever including a manual engagement section and a pivot for supporting the tool actuation lever from the control handle;
said locking lever mounted at the control handle at a location that is spaced proximally from at least part of the proximal motion member;
whereby, when the locking lever is moved to the locked state, the locking piece is slid linearly causing the partially spherical element of the proximal motion member to lockingly engage the partially spherical formed socket to thus hold the proximal motion member in the selected fixed position.

11. The surgical instrument of claim 10 wherein said rotation knob is mounted at a location that is adjacent to the locking lever.

12. The surgical instrument of claim 10 wherein said torque transmission member is disposed separate from and concentric with said proximal motion member.

13. The surgical instrument of claim 10 wherein the rotation knob and torque transmission member are separate from and independently operable from the proximal and distal motion members.

14. The surgical instrument of claim 10 wherein said locking lever is mounted at the control handle at a position that is between the proximal motion member and at least part of the tool actuation lever.

15. The surgical instrument of claim 10 wherein the slideable locking piece is disposed substantially along the central axis of the proximal motion member, and wherein said torque transmission member is disposed separate from and concentric with said proximal motion member.

16. The surgical instrument of claim 10 wherein said rotation knob is disposed at a location that is distal of the manual engagement section of the tool actuation lever, and wherein the torque transmission member has a length commensurate with the distance between the rotation knob and tool.

17. The surgical instrument of claim 16 wherein said rotation knob is mounted at a location that is proximally of at least a part of the proximal motion member.

18. The surgical instrument of claim 16 wherein the rotation knob is mounted at a location that is adjacent to the locking lever.

* * * * *